US010004278B2

(12) United States Patent
O'Donnell

(10) Patent No.: US 10,004,278 B2
(45) Date of Patent: *Jun. 26, 2018

(54) BABY HANDLING DEVICE

(71) Applicant: Laura Marie O'Donnell, Hermosa Beach, CA (US)

(72) Inventor: Laura Marie O'Donnell, Hermosa Beach, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/458,722

(22) Filed: Mar. 14, 2017

(65) Prior Publication Data

US 2017/0181478 A1    Jun. 29, 2017

Related U.S. Application Data

(63) Continuation-in-part of application No. 14/805,987, filed on Jul. 22, 2015, now Pat. No. 9,980,580, which
(Continued)

(51) Int. Cl.
*A47D 13/08* (2006.01)
*A47G 9/02* (2006.01)
(Continued)

(52) U.S. Cl.
CPC ............ *A41B 13/065* (2013.01); *A41D 1/215* (2018.01); *A41D 15/04* (2013.01); *A45C 3/00* (2013.01); *A45C 13/30* (2013.01); *A47D 13/083* (2013.01); *A47D 15/001* (2013.01); *A47G 9/0253* (2013.01); *A47G 9/083* (2013.01); *A47G 9/10* (2013.01); *A47G 9/1045* (2013.01); *A61B 5/02438* (2013.01); *A61B 5/08* (2013.01); *A61B 5/6892* (2013.01); *A61B 5/7282* (2013.01); *A61B 5/7285* (2013.01); *A61B 5/746* (2013.01); *A41B 13/06* (2013.01); *A61B 2503/04* (2013.01)

(58) Field of Classification Search
CPC ........ A47D 13/083; A47D 13/08; A47D 5/00; A47D 15/00; A47D 15/001; A47D 15/003; A47G 9/0253; A47G 9/0238; A47G 9/10
USPC ... 5/655, 657, 652, 632, 630, 494, 490, 485, 5/482
See application file for complete search history.

(56) References Cited

U.S. PATENT DOCUMENTS 3,269,621 A    8/1966 Dishart
3,667,074 A    6/1972 Emery
(Continued)

*Primary Examiner* — Robert G Santos
(74) *Attorney, Agent, or Firm* — David A. Belasco; Belasco Jacobs & Townsley, LLP

(57) ABSTRACT

A baby handling device includes a removable, washable pillow cover sized and shaped to fit over and extend from an irregular star-shaped pillow and provides at least two elongated star-point shaped extensions formed of flexible material and adapted to fold over and enclose at least a portion of a baby positioned on the cover. The cover has a closeable opening sized and shaped to permit insertion and removal of the pillow which is formed of resilient material and includes a broad center section with a central depression to receive a baby's head. A central point-shaped portion of the pillow extends upwardly from the depression and is adapted to lodge under an arm of a breast feeding mother. The pillow includes first and second side portions that surround a cavity that is sized and shaped to receive the shoulders and torso of the baby. The side portions support a baby's arms.

70 Claims, 19 Drawing Sheets

Related U.S. Application Data is a continuation-in-part of application No. 14/570,193, filed on Dec. 15, 2014, now abandoned, which is a continuation of application No. PCT/US2013/068703, filed on Nov. 6, 2013.

(51) Int. Cl.

| | | |
|---|---|---|
| A47G 9/10 | (2006.01) | |
| A41B 13/06 | (2006.01) | |
| A45C 13/30 | (2006.01) | |
| A45C 3/00 | (2006.01) | |
| A61B 5/024 | (2006.01) | |
| A61B 5/00 | (2006.01) | |
| A61B 5/08 | (2006.01) | |
| A41D 15/04 | (2006.01) | |
| A47D 15/00 | (2006.01) | |
| A47G 9/08 | (2006.01) | |
| A41D 1/215 | (2018.01) | |

(56) References Cited

U.S. PATENT DOCUMENTS

| | | | | |
|---|---|---|---|---|
| 4,173,048 | A | | 11/1979 | Varaney |
| 4,434,513 | A | | 3/1984 | Welch |
| 4,792,024 | A | | 12/1988 | Morton |
| 4,862,535 | A | | 9/1989 | Roberts |
| 5,014,376 | A | | 5/1991 | Doran |
| D328,683 | S | | 8/1992 | Kalozdi |
| 5,439,008 | A | | 8/1995 | Bowman |
| 5,546,620 | A | | 8/1996 | Matthews |
| 5,551,109 | A | * | 9/1996 | Tingley .......... A47D 13/02 128/870 |
| 5,684,460 | A | * | 11/1997 | Scanlon .......... A61B 5/113 340/573.1 |
| 6,006,381 | A | * | 12/1999 | Tandrup .......... A47D 13/08 5/637 |
| 6,038,720 | A | | 3/2000 | Matthews |
| 6,189,169 | B1 | | 2/2001 | Marcotte |
| 6,354,665 | B1 | | 3/2002 | Ross |
| 6,499,165 | B1 | | 12/2002 | Morgillo |
| 6,553,590 | B1 | * | 4/2003 | Leach .......... A47D 13/08 5/655 |
| 6,658,681 | B2 | | 12/2003 | Britto |
| 6,763,539 | B1 | | 7/2004 | Bartley |
| 7,010,821 | B1 | * | 3/2006 | Leach .......... A47D 13/083 5/636 |
| 7,127,760 | B2 | | 10/2006 | Bartley |
| 7,451,508 | B2 | | 11/2008 | Matthews Brown |
| 7,513,001 | B1 | * | 4/2009 | Leach .......... A47C 27/086 5/632 |
| 7,562,406 | B1 | * | 7/2009 | Leach .......... A47C 16/00 5/632 |
| 7,581,268 | B2 | | 9/2009 | Bell |
| 7,657,955 | B1 | | 2/2010 | Alvistur |
| 7,673,354 | B2 | | 3/2010 | Fader |
| 7,676,871 | B1 | * | 3/2010 | Leach .......... A47D 13/08 5/653 |
| 8,094,013 | B1 | * | 1/2012 | Lee .......... A61B 5/1116 340/539.15 |
| 8,191,188 | B2 | | 6/2012 | Kaplan |
| 8,365,329 | B1 | * | 2/2013 | Barsosky .......... A47D 13/083 5/632 |
| 8,393,025 | B2 | | 3/2013 | Crispino |
| 8,418,295 | B2 | * | 4/2013 | Clark .......... A47D 13/083 5/632 |
| 8,495,775 | B2 | | 7/2013 | Fair |
| 8,516,638 | B2 | | 8/2013 | Kummerfeld |
| 8,555,429 | B2 | * | 10/2013 | Leach .......... A47K 3/127 4/572.1 |
| 8,671,485 | B2 | * | 3/2014 | Smallman .......... A47D 15/008 5/413 AM |
| 9,554,659 | B2 | * | 1/2017 | Doering .......... A47D 7/04 |
| 9,693,638 | B1 | * | 7/2017 | Leach .......... A47D 13/08 |
| 9,867,480 | B2 | * | 1/2018 | Doering .......... A47D 7/04 |
| 2004/0200004 | A1 | | 10/2004 | Matthews Brown |
| 2006/0010600 | A1 | | 1/2006 | Kendy |
| 2006/0101579 | A1 | * | 5/2006 | Albers .......... A47D 13/083 5/655 |
| 2007/0022526 | A1 | * | 2/2007 | Leach .......... A01K 1/0353 4/572.1 |
| 2007/0271703 | A1 | | 11/2007 | Matthews Brown |
| 2008/0313812 | A1 | | 12/2008 | Reeves |
| 2009/0249526 | A1 | | 10/2009 | Carangelo |
| 2011/0119833 | A1 | * | 5/2011 | Clark .......... A47D 13/083 5/655 |
| 2012/0278994 | A1 | | 11/2012 | Bonzer |
| 2013/0047343 | A1 | * | 2/2013 | Barsosky .......... A47D 13/083 5/655 |
| 2013/0174316 | A1 | | 7/2013 | Smallman |
| 2014/0137324 | A1 | * | 5/2014 | Doering .......... A47D 7/04 5/93.1 |
| 2014/0173822 | A1 | * | 6/2014 | Doering .......... A47D 7/04 5/93.1 |
| 2015/0119656 | A1 | * | 4/2015 | Foster .......... A61B 5/6892 600/301 |
| 2015/0121627 | A1 | * | 5/2015 | O'Donnell .......... A41D 1/205 5/639 |
| 2015/0342264 | A1 | * | 12/2015 | O'Donnell .......... A47D 13/083 5/655 |
| 2017/0181478 | A1 | * | 6/2017 | O'Donnell .......... A41B 13/065 |

* cited by examiner

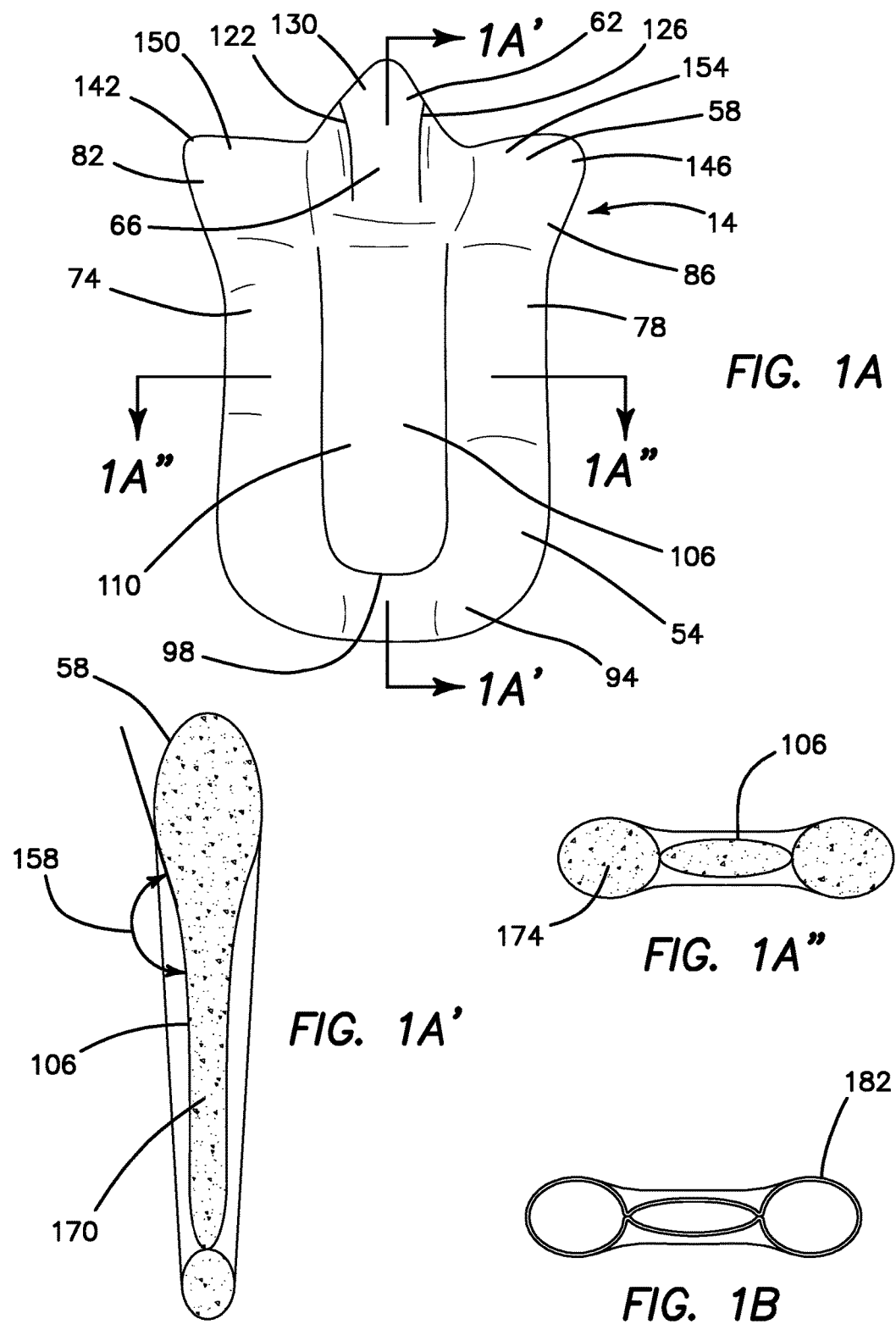

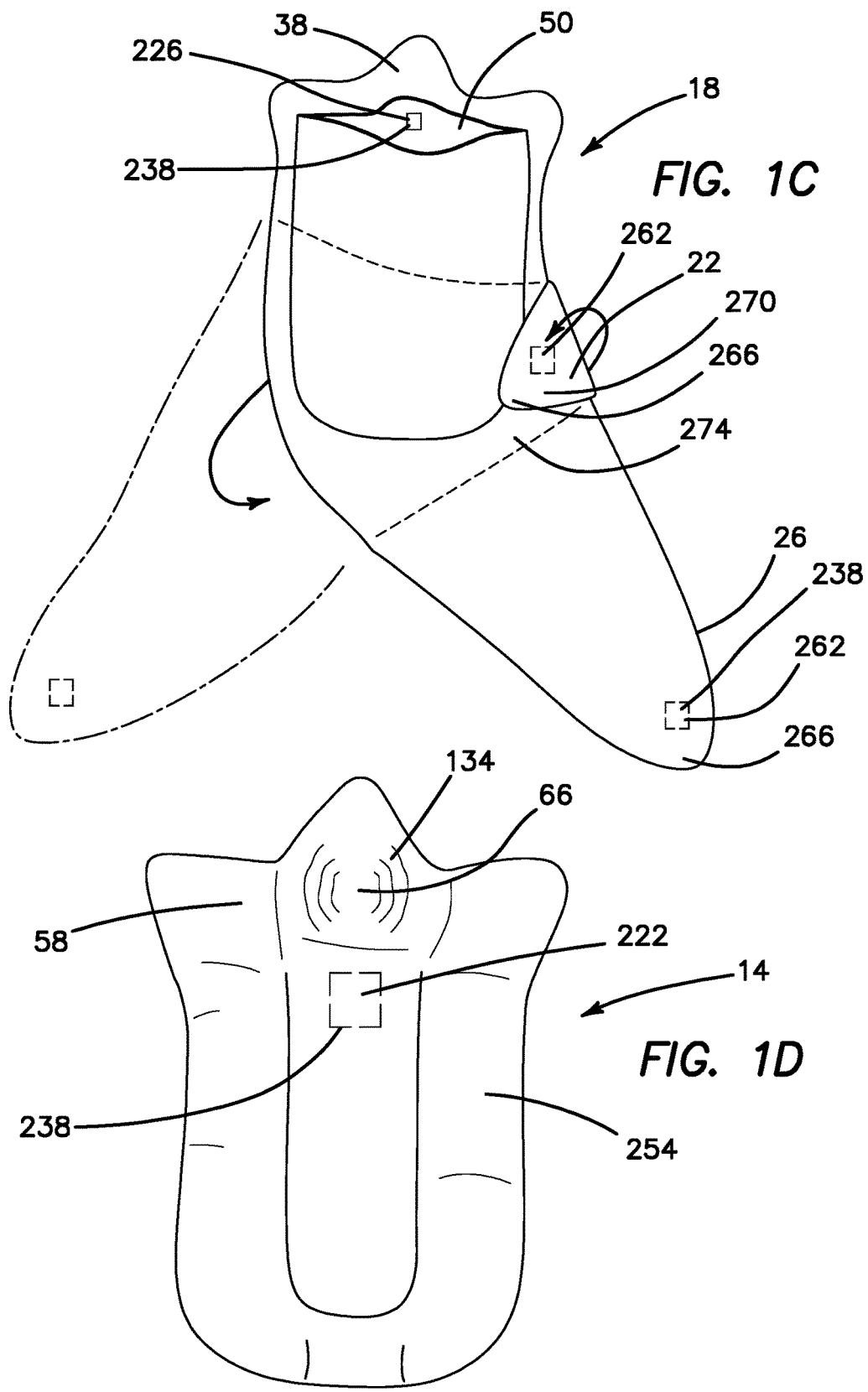

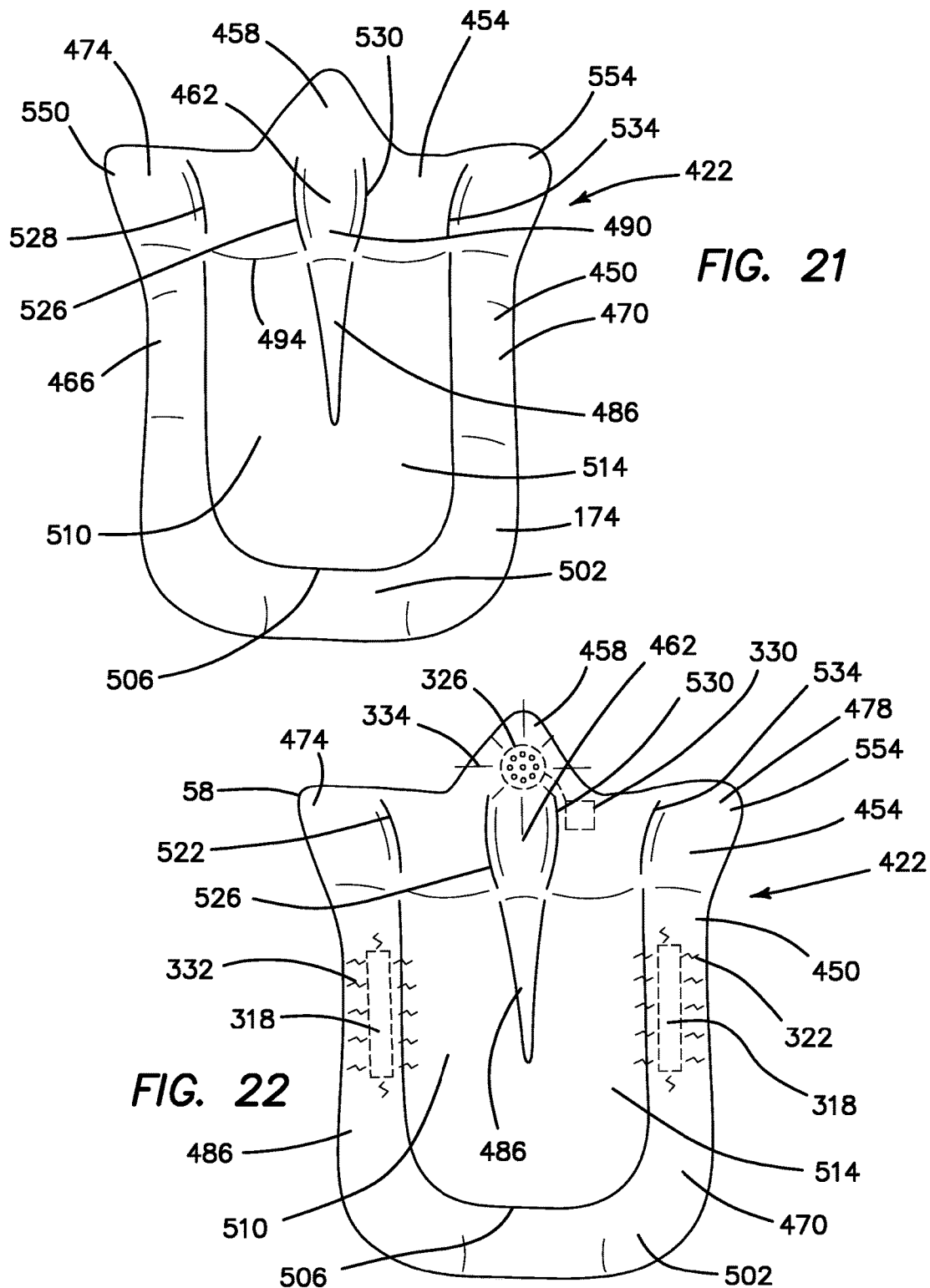

BABY HANDLING DEVICE

RELATED APPLICATION

The instant application is a continuation-in-part of U.S. application Ser. No. 14/805,987, filed Jul. 22, 2015, which is a continuation-in-part of U.S. application Ser. No. 14/570,193, filed Dec. 15, 2014 and currently abandoned, which is a continuation of PCT/US2013/068703, filed Nov. 6, 2013 and currently expired. The disclosure of these applications is hereby incorporated by reference in their entirety.

FIELD OF INVENTION

This invention relates to the field of infant care items and more specifically to a combination device for baby swaddling, support during breast feeding and other baby handling functions and use as an infant sleeping bag.

BACKGROUND OF THE INVENTION

Newborn children and infants require special and specific care to avoid injury when handled for feeding or even when left to rest. As infant neck muscles are just developing, it is critical that the baby's head be supported when the baby is leaned backward as it might be for feeding. When infants are placed in cribs to sleep, it is important that they are prevented from turning themselves face down where they could smother against the surface of the crib. For this reason, a means to prevent the infant from using his or her arms while sleeping is necessary. To address this problem, various techniques and devices have been developed to swaddle the infant and cause it to sleep safely on his or her back. It is also important that the surface provided for the baby to sleep upon be so shaped as to avoid the baby's head being inclined too far forward which could close off the airway of the baby. As the baby grows, it is often desirable to have a portable, ready-made bed or sleeping bag for the baby to use when away from home. Various solutions to these problems have been proposed.

U.S. Pat. No. 7,127,760, issued to Bartley et al. is directed to a nursing pillow and methods. This device, a support pillow, includes a horseshoe shaped pillow body disposed around a well region. A support member is fixed in a portion of the well and is provided to support some or all of an object resting on the pillow. Construction of the pillow can vary with the top and bottom pieces being cut into U-shaped pieces and sewn together or two continuous pieces and sewn together with a seam forming the interior section of the U-shape providing structure for a continuous transition from the pillow sections to the support member. Pockets may be included on the outer periphery of the pillow.

U.S. Pat. No. 7,673,354, issued to Fader is directed to a baby sleeping pouch method and apparatus. This device is a pouch. A baby may be placed on a wedge pillow and positioned with in the pouch. Additionally, it is suggested that the baby may be swaddled in a blanket prior to insertion into the pouch.

U.S. Pat. No. 8,393,025, issued to Crispino et al. illustrates a bed covering system. This system includes a lower sheet and an upper sheet. At least one expandable flap joins the edges of the lower and upper sheets. A pocket may be supplied on the lower sheet near the pillow or pillow encasement.

U.S. Pat. No. 6,499,165, issued to Morgillo discloses an infant safety device. This safety device includes a U-shaped pillow support portion and a harness portion. A pillow case may be provided to cover the U-shaped pillow. In this embodiment, the harness portion is fixed to the pillow case.

U.S. Pat. No. 8,516,638, issued to Kummerfeld et al. is directed to a feeding pillow with a removable surface. The feeding pillow is generally U-Shaped or C-Shaped. The pillow has a pocket. A support member is positioned in the pocket and may be removed through an opening.

It is an objective of the present invention to provide a convenient baby support for breast feeding and other purposes in which the baby's head must be supported. It is another objective to provide a sleeping surface that prevents excessive forward inclination of the baby's head when sleeping on its back. It is a further objective to provide a device for constraining a baby's arms while resting or sleeping. It is a still further objective of the invention to provide a compact infant sleeping bag for use when traveling. It is yet a further objective to provide a baby handling device that can be easily maintained in a sanitary condition. Finally, it is an objective of the present invention to provide a baby handling device that is inexpensive, attractive, light weight and easily manufactured.

While some of the objectives of the present invention are disclosed in the prior art, none of the inventions found include all of the requirements identified.

SUMMARY OF THE INVENTION

The present invention addresses all of the deficiencies of prior art baby handling device inventions and satisfies all of the objectives described above.

(1) A baby handling device may be constructed from the following components. An irregular star-shaped pillow is provided. A removable, washable pillow cover is provided. The cover is sized and shaped to fit over and extend from the irregular star-shaped pillow and provides at least two elongated star-point shaped extensions. The extensions are formed of flexible material and adapted to fold over and enclose at least a portion of a baby positioned on the cover. An upper portion of the cover is adapted to support and control movement of the baby's head when the elongated star-point shaped extensions are wrapped around the baby and fastened to an outer surface of the cover. The cover has a closeable opening sized and shaped to permit insertion and removal of the pillow.

(2) In a variant of the invention, the irregular star-shaped pillow is formed of resilient material and further includes a broad upper section sized and shaped to support the baby's head. A central point-shaped portion extends upwardly from a center point of the upper section. The point-shaped portion is adapted to lodge under an arm of a breast feeding mother. First and second side sections are provided. The side sections are joined to first and second ends of the upper section and are sized and shaped to support the baby's arms. A lower section is provided. The lower section is joined to the first and second side sections and is sized and shaped to provide a stop for the baby's feet. The stop prevents the baby from sliding downwardly from the center section. The broad upper section, the side portions and the lower section surround a center section. The center section provides a support platform for the baby and works with the broad upper section to control an inclination of the baby's head when the baby is on its back and located upon the pillow.

(3) In another variant, the irregular star-shaped pillow further includes first and second dividers. The dividers are located on either side of a center point of the upper section and serve to urge the baby's head toward the center point. The pillow has a reduced amount of stuffing between the dividers.

(4) In still another variant, the irregular star-shaped pillow further includes a central depression. The central depression is located at a center point of the upper section and serves to control a position of the baby's head on the upper section and to limit inclination of the baby's head.

(5) In yet another variant, the irregular star-shaped pillow further includes first and second point-shaped portions. The first and second point-shaped portions extend outwardly from the first and second ends of the upper section.

(6) In a further variant, an included angle formed between the broad upper section and the center section is greater than or equal to 150 degrees.

(7) In still a further variant, the resilient material is selected from the group that includes cotton batting, polyester batting, foam rubber, memory foam, memory foam segments and an inflatable bladder.

(8) In yet a further variant, the removable, washable pillow cover is formed of material selected from the group that includes terrycloth, cotton, polyester, cotton-polyester blends, wool, rayon, bamboo, satin weave fabrics and sateen weave fabrics.

(9) In another variant of the invention, the irregular star-shaped pillow further includes at least one fastening device and the cover includes at least one mating fastening device for securing the pillow within the cover.

(10) In still another variant, the fastening device is selected from the group that includes tie strings, hook and eye combinations, hooking and looping devices, buttons, snaps and zippers.

(11) In yet another variant, the irregular star-shaped pillow is formed of impermeable material.

(12) In a further variant, the removable cover further includes a storage pocket.

(13) In still a further variant, at least one point attachment device is provided. The point attachment device provides attachment for a distal end of the elongated star-point shaped extension to at least one location on an exterior surface of the cover, thereby adapting the extension to secure the baby in a predetermined position.

(14) In yet a further variant, the point attachment device in selected from the group that includes tie strings, hook and eye combinations, hooking and looping devices, buttons, snaps and zippers.

(15) In another variant of the invention, the point attachment device is located to secure the baby in a first position. The first position attaches the extension at shoulder height for the baby. The first position constrains arms of the baby.

(16) In still another variant, the point attachment device is located to secure the baby in a second position. The second position attaches the extension at abdomen height for the baby. The second position permits movement of arms of the baby.

(17) In yet another variant, at least one accessory fastening device is provided. The accessory fastening device is attached to the cover where the cover extends over any of the central point-shaped portion and the first and second point-shaped portions of the irregular star-shaped pillow, the accessory fastening device providing an attachment point for toys, pacifiers and other accessories.

(18) In a further variant, the irregular star-shaped pillow further includes an electrically operated vibrating element. The element causes the device to provide a soothing vibration to induce sleep in the baby.

(19) In still a further variant, the irregular star-shaped pillow further includes at least one loudspeaker and electrically operated sound source. The sound source provides music to provide a calming environment for the baby.

(20) In yet a further variant, a combination fastening and carrying strap is provided. The strap serves to hold the device in a compact bundle and to provide a carrying handle. The strap is attached to the removable cover with any of stitching, hook and eye combinations, buttons, snaps, looping and hooking fasteners and zippers.

(21) In another variant of the invention, the removable cover includes a plurality of attachment devices. The attachment devices secure the elongated star-point shaped extensions about the irregular star-shaped pillow in a compact bundle.

(22) In still another variant, the combination fastening and carrying strap provides a mounting for baby toys and accessories and is adapted to secure the baby to the irregular star-shaped pillow.

(23) In yet another variant, the elongated star-point shaped extension of the cover is adapted to provide a privacy shield during nursing.

(24) In a further variant, a carrying bag is provided. The bag is sized and shaped to enclose any of the removable, washable pillow cover, the irregular star-shaped pillow and baby supplies.

(25) In still a further variant, a carrying strap is provided.

(26) In yet a further variant, the carrying bag further includes at least one pocket.

(27) In another variant of the invention, a heartbeat monitoring system is provided. The heartbeat monitoring system further includes an alarm system to indicate absence of a baby's heartbeat.

(28) In still another variant, the irregular star-shaped pillow further includes a weight sensing system to determine if the baby is positioned upon the pillow and the heartbeat monitoring system should be activated.

(29) In yet another variant, a battery life indicator is provided. The battery life indicator confirms that the heartbeat monitoring system will receive sufficient power for a predetermined period of time once the weight sensing system determines that the baby is disposed upon the pillow.

(30) In still another variant, the irregular star-shaped pillow further includes a respiration monitoring system. The respiration monitoring system further includes an alarm system to indicate absence of a baby's breathing.

(31) In yet another variant, the irregular star-shaped pillow further includes a weight sensing system to determine if the baby is positioned upon the pillow and the respiration monitoring system should be activated.

(32) In a further variant, a battery life indicator is provided. The battery life indicator confirms that the respiration monitoring system will receive sufficient power for a predetermined period of time once the weight sensing system determines that the baby is disposed upon the pillow.

(33) In still a further variant, the irregular star-shaped pillow further includes a motion detection system. The motion detection system further includes an alarm system to indicate absence of a baby's movement.

(34) In yet a further variant, the irregular star-shaped pillow further includes a weight sensing system to determine if the baby is positioned upon the pillow and the motion detection system should be activated.

(35) In still a further variant, a battery life indicator is provided. The battery life indicator confirms that the motion detection system will receive sufficient power for a predetermined period of time once the weight sensing system determines that the baby is disposed upon the pillow.

(36) In yet a further variant, an irregular star-shaped pillow is provided. A removable, washable pillow cover is provided. The cover is sized and shaped to fit over and extend from the irregular star-shaped pillow and provides at least two elongated star-point shaped extensions. The extensions are formed of flexible material and adapted to fold over and enclose at least a portion of two babies positioned on the cover. An upper portion of the cover is adapted to support and control movement of the babies' heads when the elongated star-point shaped extensions are wrapped around the babies and fastened to an outer surface of the cover. The cover has a closeable opening sized and shaped to permit insertion and removal of the pillow.

(37) In another variant of the invention, the irregular star-shaped pillow is formed of resilient material and further includes a broad upper section sized and shaped to support the babies' heads. A central point-shaped portion extends upwardly from a center point of the upper section. The point-shaped portion is adapted to lodge under an arm of a breast feeding mother. First and second side sections are provided. The side sections are joined to first and second ends of the upper section and are sized and shaped to support outer arms of the babies. A center arm rest is provided. The center arm rest is joined to a center point of a bottom edge of the upper section and is sized and shaped to support inner arms of the babies. A lower section is provided. The lower section is joined to the first and second side sections and is sized and shaped to provide a stop for the babies' feet. The stop prevents the babies from sliding downwardly from the center section. The broad upper section, the side portions, the center arm rest and the lower section surround the first and second center sections. The center sections provide support platforms for the babies and work with the broad upper section to control an inclination of the babies' heads when the babies are disposed on their backs upon the pillow.

(38) In still another variant, the irregular star-shaped pillow further includes first, second, third and fourth dividers. The dividers are located on either side of a center point of the upper section and serve to control positioning of the babies' heads on the upper section.

(39) In yet another variant, the irregular star-shaped pillow further includes first and second depressions. The first and second depressions are disposed on either side of a center point of the upper section and serve to control positions of the babies' heads on the upper section to limit inclination of the babies' heads.

(40) In a further variant, the irregular star-shaped pillow further includes first and second point-shaped portions. The first and second point-shaped portions extend outwardly from the first and second ends of the upper section.

(41) In still a further variant, an included angle formed between the broad upper section and either of the first and second center sections is greater than or equal to 150 degrees.

(42) In yet a further variant, the resilient material is selected from the group that includes cotton batting, polyester batting, foam rubber, memory foam, memory foam segments and an inflatable bladder.

(43) In another variant of the invention, the removable, washable pillow cover is formed of material selected from the group includes terrycloth, cotton, polyester, cotton-polyester blends, wool, rayon, bamboo, satin weave fabrics and sateen weave fabrics.

(44) In still another variant, the irregular star-shaped pillow further includes at least one fastening device. The cover includes at least one mating fastening device for securing the pillow within the cover.

(45) In yet another variant, the fastening device is selected from the group that Includes tie strings, hook and eye combinations, hooking and looping devices, buttons, snaps and zippers.

(46) In a further variant, the irregular star-shaped pillow is formed of impermeable material.

(47) In still a further variant, the removable cover further includes a storage pocket.

(48) In yet a further variant, at least one point attachment device is provided. The point attachment device provides attachment for a distal end of the elongated star-point shaped extension to at least one location on an exterior surface of the cover, thereby adapting the extension to secure the babies in predetermined positions.

(49) In another variant of the invention, the point attachment device in selected from the group includes tie strings, hook and eye combinations, hooking and looping devices, buttons, snaps and zippers.

(50) In still another variant, the point attachment device is disposed to secure the babies in a first position. The first position attaches the extension at shoulder height for the babies. The first position constrains the arms of the babies.

(51) In yet another variant, the point attachment device is disposed to secure the babies in a second position. The second position attaches the extension at abdomen height for the babies. The second position permits movement of the arms of the babies.

(52) In a further variant, at least one accessory fastening device is provided. The accessory fastening device is attached to the cover where the cover extends over any of the central point-shaped portion and the first and second point-shaped portions of the irregular star-shaped pillow. The accessory fastening device provides an attachment point for toys, pacifiers and other accessories.

(53) In still a further variant, the irregular star-shaped pillow further includes an electrically operated vibrating element. The element causes the device to provide a soothing vibration to induce sleep in the babies.

(54) In yet a further variant, the irregular star-shaped pillow further includes at least one loudspeaker and electrically operated sound source. The sound source provides music to provide a calming environment for the babies.

(55) In another variant of the invention, a combination fastening and carrying strap is provided. The strap serves to hold the device in a compact bundle and to provide a carrying handle. The strap is attached to the removable cover with any of stitching, snaps, hook and eye combinations, buttons, snaps, looping and hooking fasteners and zippers.

(56) In still another variant, the removable cover includes a plurality of attachment devices. The attachment devices secure the elongated star-point shaped extensions about the irregular star-shaped pillow in a compact bundle.

(57) In yet another variant, the combination fastening and carrying strap provides a mounting for baby toys and accessories and is adapted to secure the babies to the irregular star-shaped pillow.

(58) In a further variant, the elongated star-point shaped extension of the cover is adapted to provide a privacy shield during nursing.

(59) In still a further variant, a carrying bag is provided. The bag is sized and shaped to enclose any of the removable, washable pillow cover, the irregular star-shaped pillow and baby supplies.

(60) In yet a further variant, a carrying strap is provided.

(61) In another variant of the invention, the carrying bag further includes at least one pocket.

(62) In still another variant, the irregular star-shaped pillow further includes a heartbeat monitoring system. The heartbeat monitoring system further includes an alarm system to indicate absence of either of the babies' heartbeats.

(63) In yet another variant, the irregular star-shaped pillow further includes a weight sensing system to determine if either of the babies is positioned upon the pillow and the heartbeat monitoring system should be activated.

(64) In a further variant, a battery life indicator is provided. The battery life indicator confirms that the heartbeat monitoring system will receive sufficient power for a predetermined period of time once the weight sensing system determines that either of the babies is disposed upon the pillow.

(65) In still a further variant, the irregular star-shaped pillow further includes a respiration monitoring system. The respiration monitoring system further includes an alarm system to indicate absence of either of the babies' breathing.

(66) In yet a further variant, the irregular star-shaped pillow further includes a weight sensing system to determine if either of the babies is positioned upon the pillow and the respiration monitoring system should be activated.

(67) In another variant of the invention, a battery life indicator is provided. The battery life indicator confirms that the respiration monitoring system will receive sufficient power for a predetermined period of time once the weight sensing system determines that either of the babies is disposed upon the pillow.

(68) In still another variant, the irregular star-shaped pillow further includes a motion detection system. The motion detection system further includes an alarm system to indicate absence of either of the babies' movement.

(69) In yet another variant, the irregular star-shaped pillow further includes a weight sensing system to determine if either of the babies is positioned upon the pillow and the motion detection system should be activated.

(70) In a final variant of the invention, a battery life indicator is provided. The battery life indicator confirms that the motion detection system will receive sufficient power for a predetermined period of time once the weight sensing system determines that either of the babies is disposed upon the pillow.

DESCRIPTION OF THE DRAWINGS

FIG. 1A is a plan view of the irregular star-shaped pillow of the FIG. 1 embodiment illustrating first and second dividers in the upper section of the pillow;

FIG. 1A' is a cross-sectional view of the pillow of FIG. 1A taken along the line 1A'-1A' illustrating a foam rubber core;

FIG. 1A" is a cross-sectional view of the pillow of FIG. 1A taken along the line 1A"-1A" illustrating a memory foam core;

FIG. 1B is a cross-sectional view of a pillow formed as an inflatable bladder;

FIG. 1C is a plan view of the pillow cover illustrating attachment of the elongated star-point shaped extensions to the pillow cover with hooking and looping fastening devices;

FIG. 1D is a plan view of the pillow of the FIG. 1 embodiment illustrating the central depression in the upper section of the pillow;

FIG. 21 is a plan view of a two baby embodiment of the pillow illustrating first, second, third and fourth dividers;

FIG. 22 is a plan view of a two baby embodiment of the pillow illustrating a speaker, sound source and vibrating elements;

DETAILED DESCRIPTION OF THE PREFERRED EMBODIMENT

Figure 1:
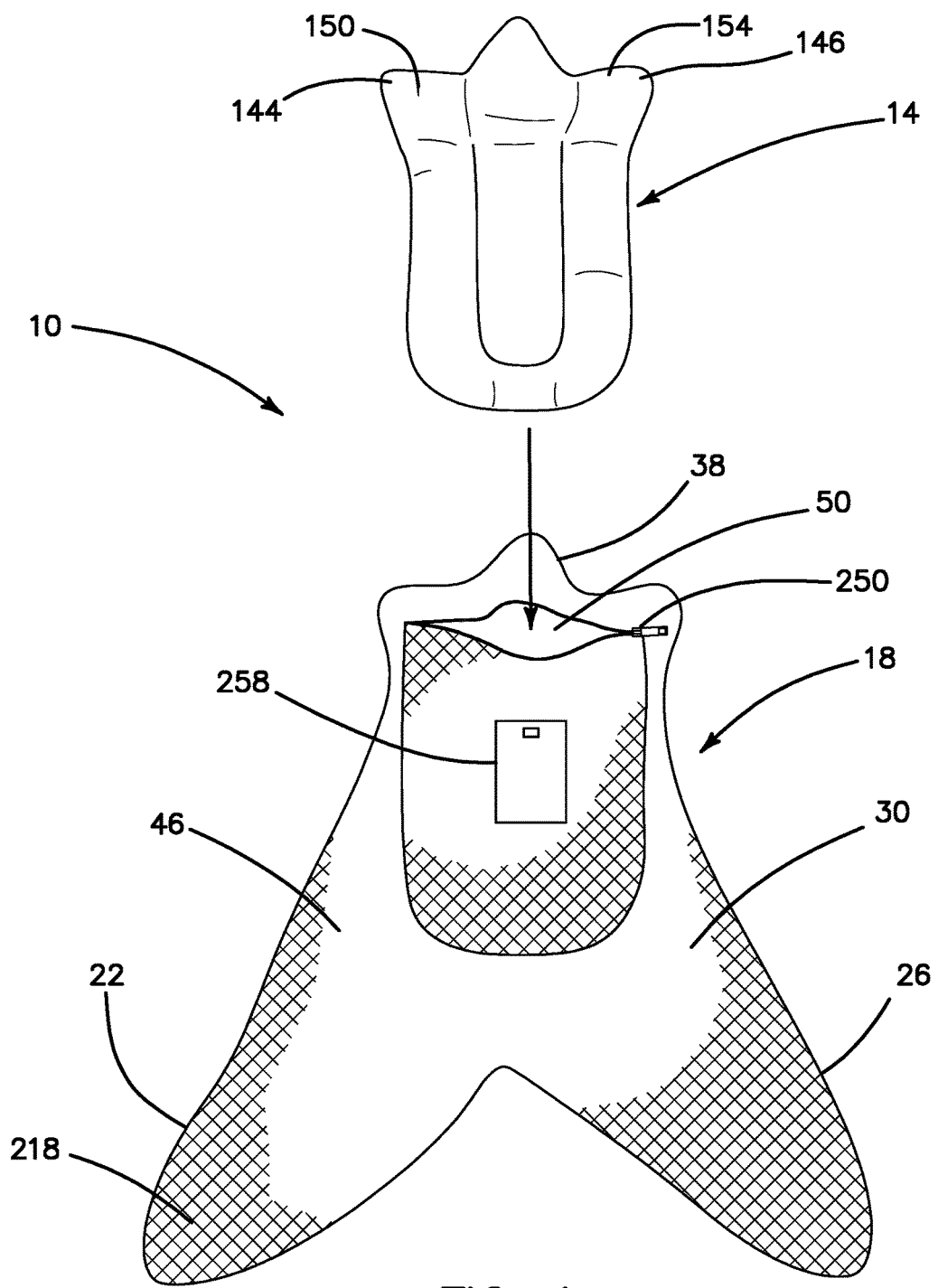
FIG. 1 is a plan view of the preferred embodiment of the invention illustrating the irregular star-shaped pillow, the pillow cover and pocket closure for the pillow in the cover.

The present invention addresses all of the deficiencies of prior art baby handling device inventions and satisfies all of the objectives described above.

(1) A baby handling device 10, as illustrated in FIGS. 1-15, may be constructed from the following components. An irregular star-shaped pillow 14 is provided. A removable, washable pillow cover 18 is provided. The cover 18 is sized and shaped to fit over and extend from the irregular star-shaped pillow 14 and provides at least two elongated star-point shaped extensions 22, 26. The extensions 22, 26 are formed of flexible material 30 and adapted to fold over and enclose at least a portion of a baby 34 positioned on the cover 18. An upper portion 38 of the cover 18 is adapted to support and control movement of the baby's head 42 when the elongated star-point shaped extensions 22, 26 are wrapped around the baby 34 and fastened to an outer surface 46 of the cover 18. The cover 18 has a closeable opening 50 sized and shaped to permit insertion and removal of the pillow 14.

Figure 8:
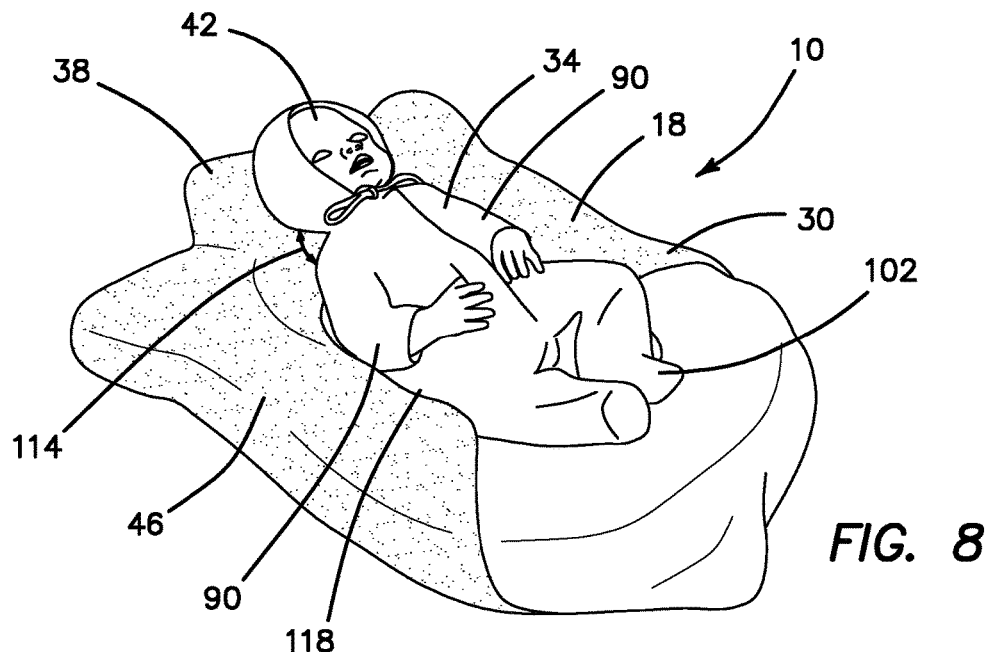
FIG. 8 is a perspective view of a baby disposed supine on the baby handling device illustrating the foot stop of the pillow controlling downward movement of the baby on the pillow.
Figure 12:
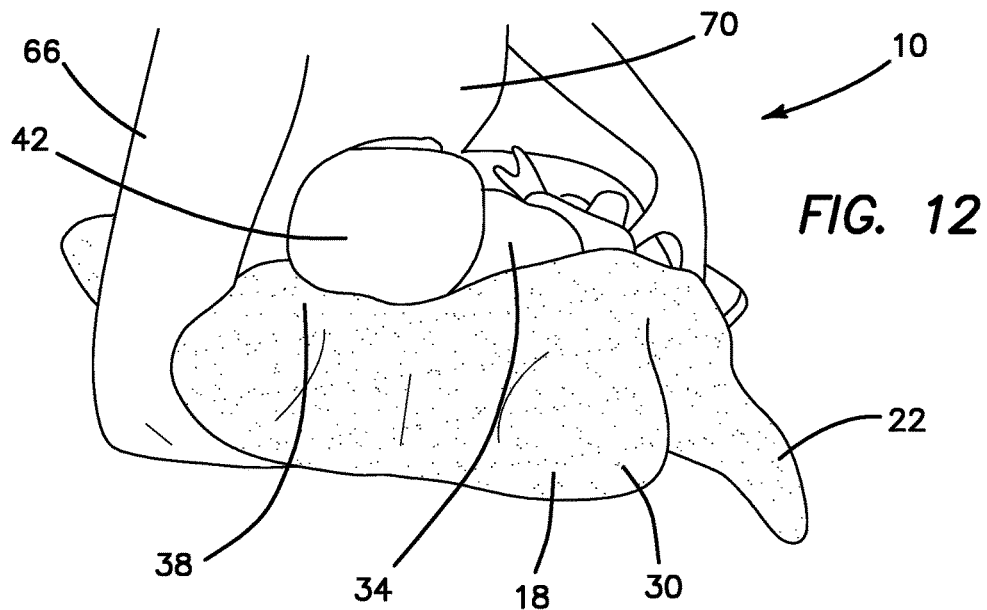
FIG. 12 is a perspective view of a baby disposed supine on the baby handling device illustrating preparation for breast feeding.
Figure 13:
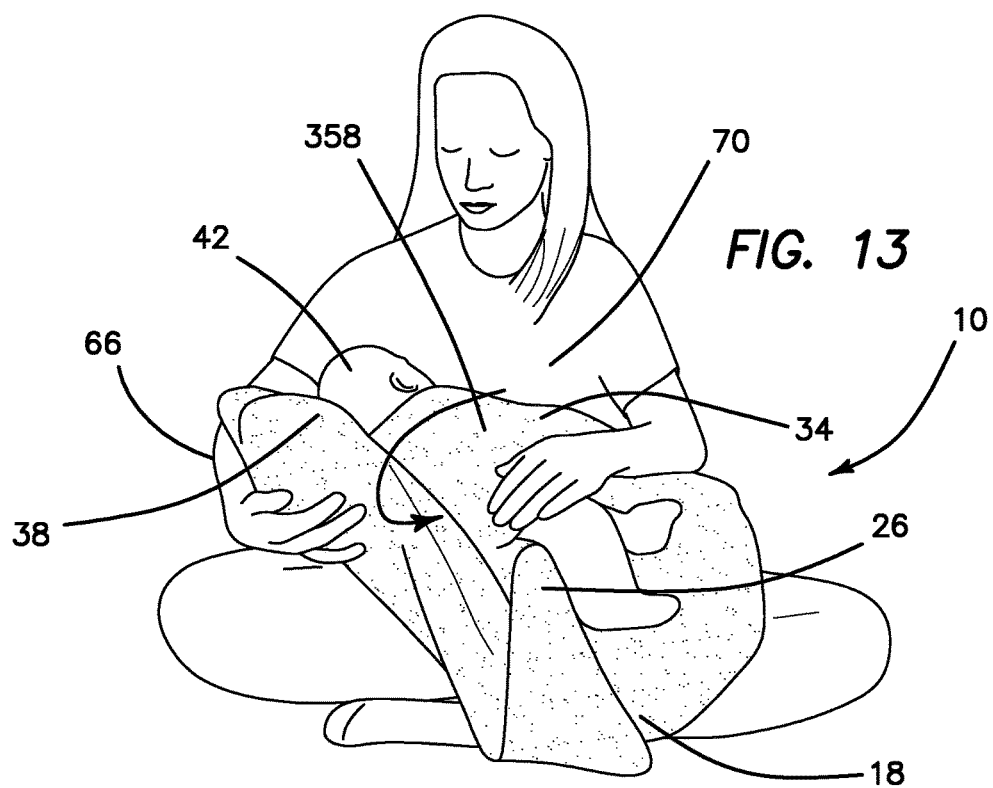
FIG. 13 is a perspective view of a baby disposed supine on the baby handling device illustrating the breast feeding position.
Figure 14:
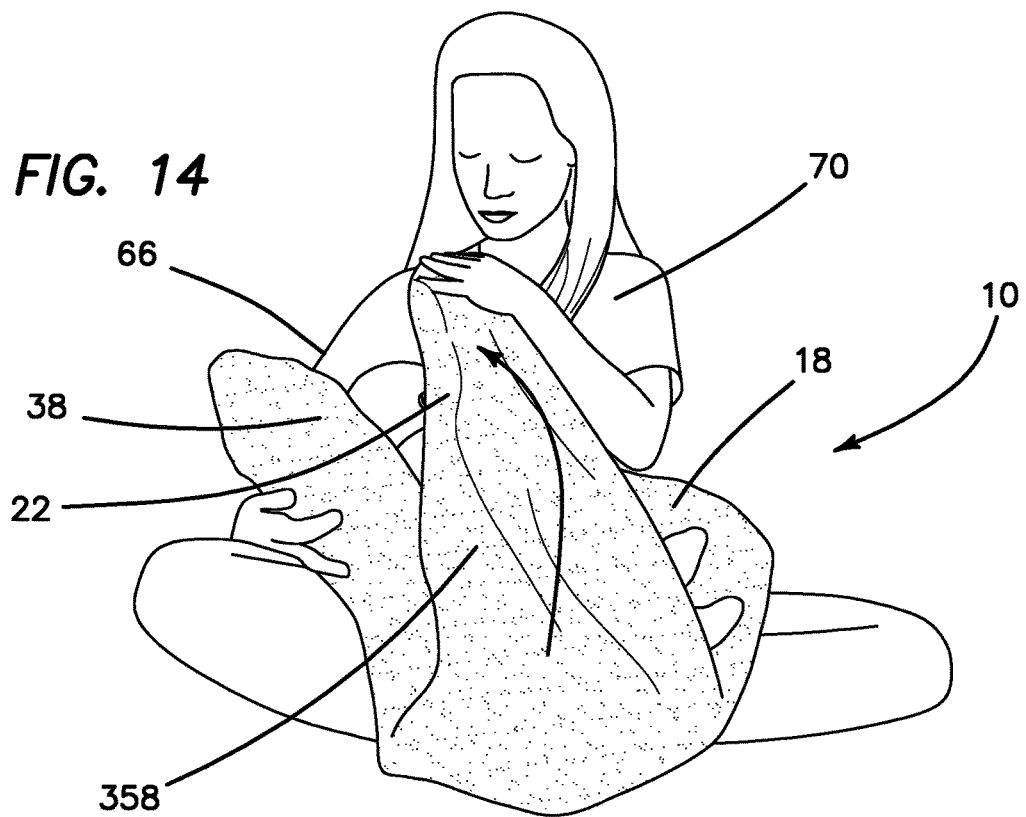
FIG. 14 is a perspective view of a baby disposed supine on the baby handling device illustrating use of one of the elongated star-point shaped extensions as a privacy shield for breast feeding.

(2) In a variant of the invention, as illustrated in FIGS. 1A and 1D-1F, the irregular star-shaped pillow 14 is formed of resilient material 54 and further includes a broad upper section 58 sized and shaped to support the baby's head 42. A central point-shaped portion 62 extends upwardly from a center point 66 of the upper section 58. The point-shaped portion 62 is adapted to lodge under an arm 66 of a breast feeding mother 70, as illustrated in FIGS. 12-14. As illustrated in FIGS. 1A and 1C-1F, first 74 and second 78 side sections are provided. The side sections 74, 78 are joined to first 82 and second 86 ends of the upper section 58 and are sized and shaped to support the baby's arms 90 as illustrated in FIG. 8. A lower section 94 is provided. The lower section 94 is joined to the first 74 and second 78 side sections and is sized and shaped to provide a stop 98 for the baby's feet 102. The stop 98 prevents the baby 34 from sliding downwardly from a center section 106. The broad upper section 58, the side sections 74, 78 and the lower section 94 surround the center section 106.

The center section 106 provides a support platform 110 for the baby 34 and works with the broad upper section 58 to control an inclination 114 of the baby's head 42 when the baby 34 is on its back 118 and located upon the pillow 14.

(3) In another variant, as illustrated in FIG. 1A, the irregular star-shaped pillow 14 further includes 122 first and second 126 dividers. The dividers 122, 126 are located on either side of the center point 66 of the upper section 58 and serve to urge the baby's head 42 toward the center point 66. The pillow 14 has a reduced amount of stuffing 130 between the dividers 122, 126.

(4) In still another variant, as illustrated in FIG. 1D, the irregular star-shaped pillow 14 further includes a central depression 134. The central depression 134 is located at the center point 66 of the upper section 58 and serves to control a position of the baby's head 42 on the upper section 58 and to limit inclination 114 of the baby's head 42, as illustrated in FIG. 8.

(5) In yet another variant, as illustrated in FIGS. 1 and 1A, the irregular star-shaped pillow 14 further includes first 142 and second 146 point-shaped portions. The first 142 and second 146 point-shaped portions extend outwardly from the first 82 and second 86 ends of the upper section 58.

(6) In a further variant, as illustrated in FIG. 1A' an included angle 158 formed between the broad upper section 58 and the center section 106 is greater than or equal to 150 degrees.

(7) In still a further variant, as illustrated in FIGS. 1, 1A'-1B, the resilient material 54 is selected from the group that includes cotton batting 162, polyester batting 166, foam rubber 170, memory foam 174, memory foam segments 178 and an inflatable bladder 182.

(8) In yet a further variant, the removable, washable pillow cover 18 is formed of material selected from the group that includes terrycloth (not shown), cotton (not shown), polyester (not shown), cotton-polyester blends (not shown), wool (not shown), rayon (not shown), bamboo (not shown), satin weave fabrics (not shown) and sateen weave fabrics 218.

(9) In another variant of the invention, as illustrated in FIGS. 1, 1C and 1D, the irregular star-shaped pillow 14 further includes at least one fastening device 222 and the cover 18 includes at least one mating fastening device 226 for securing the pillow 14 within the cover 18.

(10) In still another variant, the fastening device 222 is selected from the group that includes tie strings 230, hook and eye combinations (not shown), hooking and looping devices 238, buttons 242, snaps (not shown) and zippers 250.

(11) In yet another variant, the irregular star-shaped pillow 14 is formed of impermeable material 254.

(12) In a further variant, as illustrated in FIG. 1B, the removable cover 18 further includes a storage pocket 258.

(13) In still a further variant, as illustrated in FIG. 1C, at least one point attachment device 262 is provided. The point attachment device 262 provides attachment for a distal end 266 of the elongated star-point shaped extension 22, 26 to at least one location 270 on an exterior surface 274 of the cover 18, thereby adapting the extension 22, 26 to secure the baby 34 in a predetermined position 278, as illustrated in FIGS. 4 and 5.

(14) In yet a further variant, the point attachment device 262 is selected from the group that includes tie strings 230, hook and eye combinations 234, hooking and looping devices 238, buttons 242, snaps 246 and zippers 250.

Figure 4:
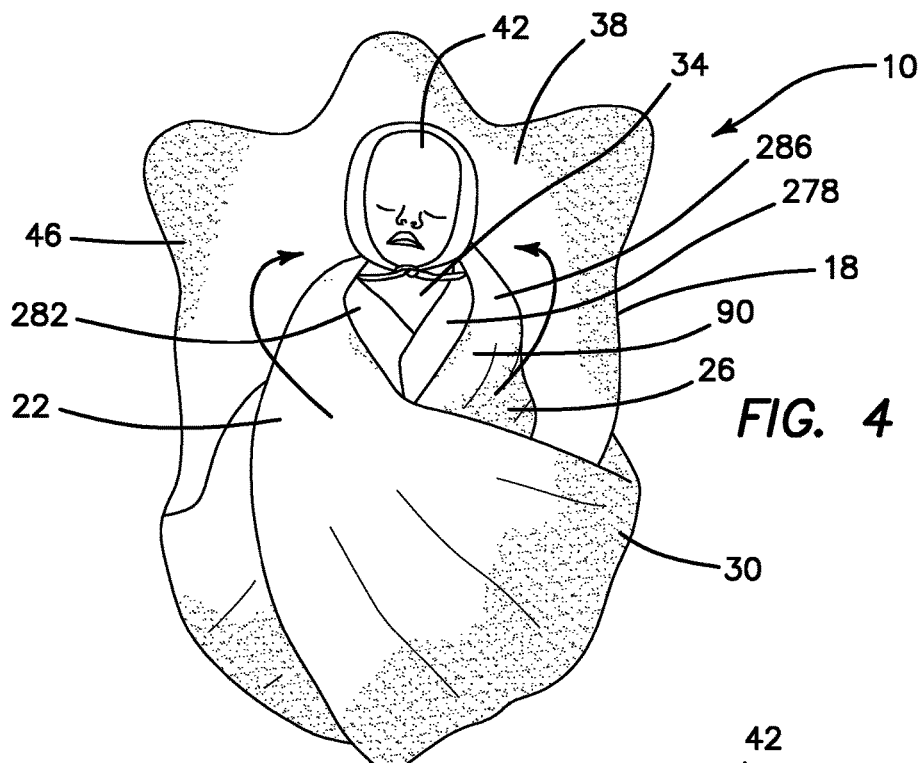
FIG. 4 is a perspective view of a baby disposed on the baby handling device with the elongated star-point shaped extensions configured in the first position.

(15) In another variant of the invention, as illustrated in FIG. 4, the point attachment device 262 is located to secure the baby 34 in a first position 282. The first position 282 attaches the extension 22, 26 at shoulder height 286 for the baby 34. The first position 282 constrains arms 90 of the baby 34.

Figure 5:
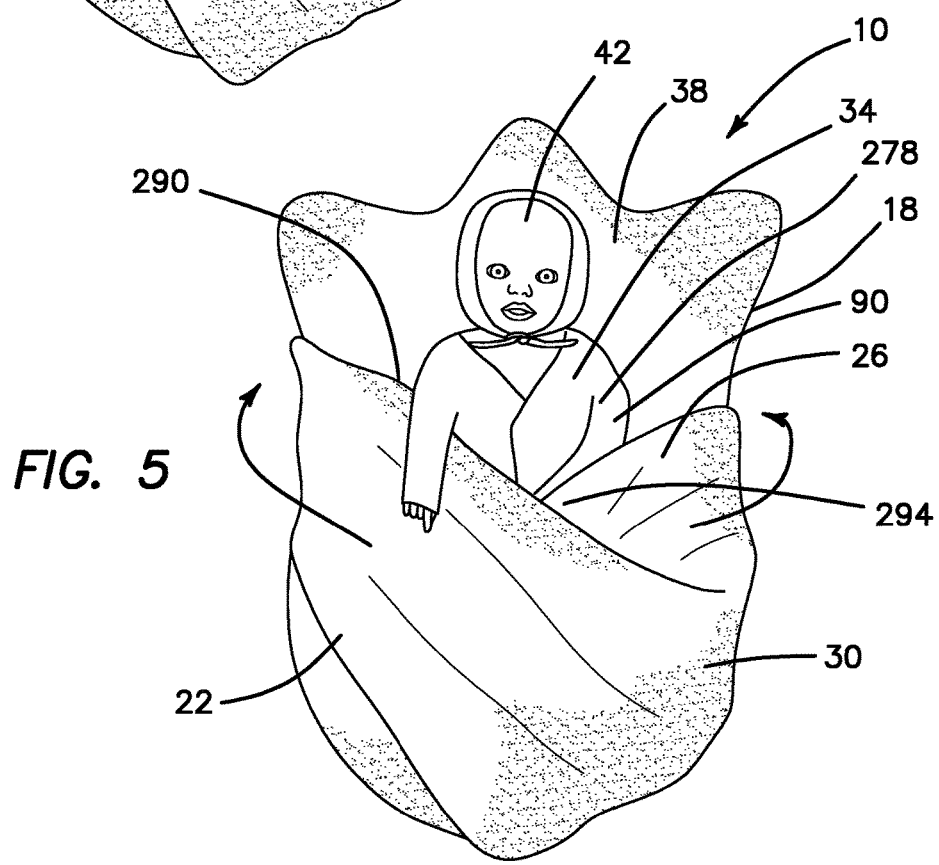
FIG. 5 is a perspective view of a baby disposed on the baby handling device with the elongated star-point shaped extensions configured in the second position.
Figure 6:
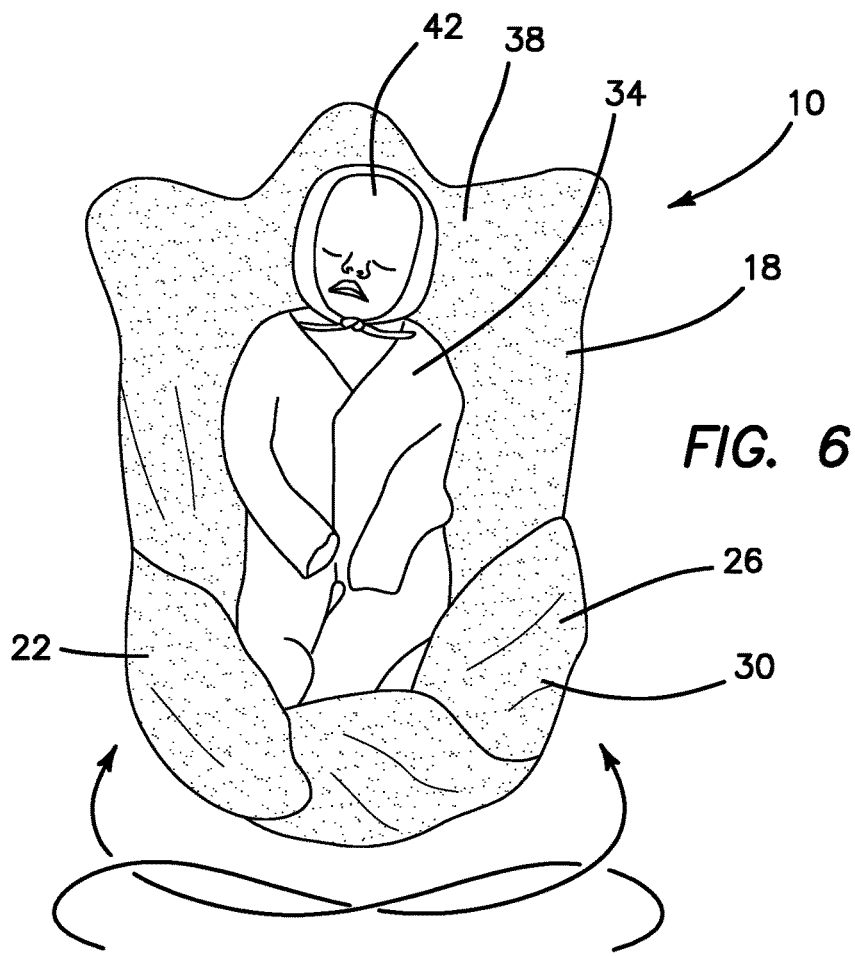
FIG. 6 is a perspective view of a baby disposed on the baby handling device with the elongated star-point shaped extensions configured to secure the baby's feet.
Figure 7:
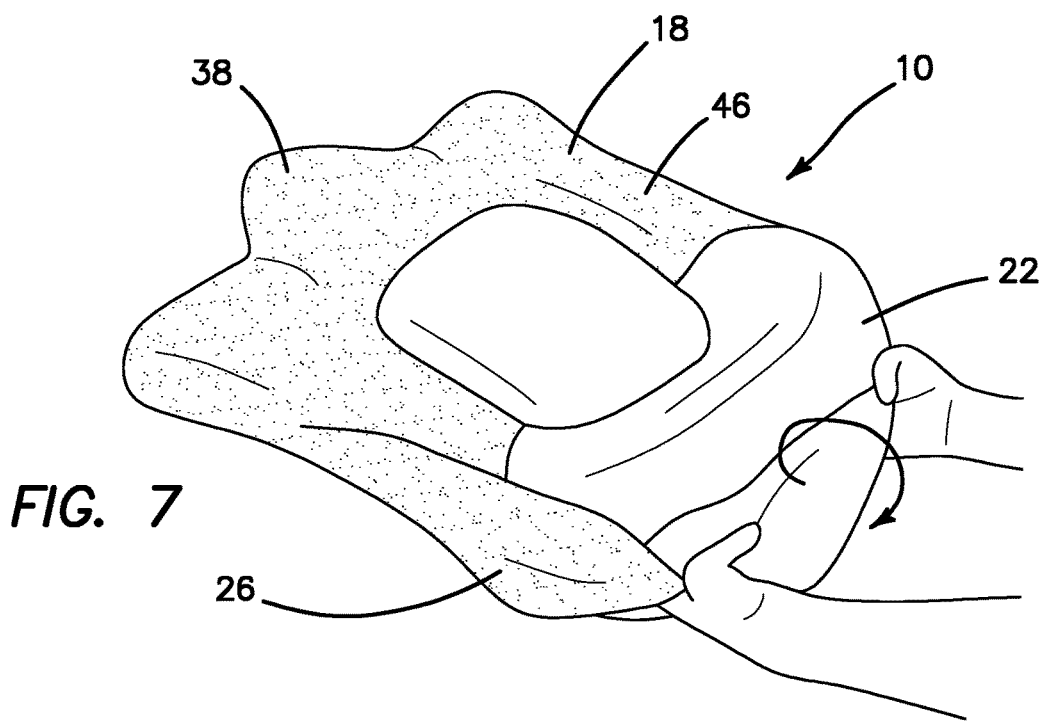
FIG. 7 is a perspective view of the pillow illustrating the disposal of the elongated star-point shaped extensions behind and beneath the pillow.

(16) In still another variant, as illustrated in FIG. 5, the point attachment device 262 is located to secure the baby 34 in a second position 290. The second position 290 attaches the extension 22, 26 at abdomen height 294 for the baby 34. The second position 290 permits movement of arms 90 of the baby 34.

Figure 2:
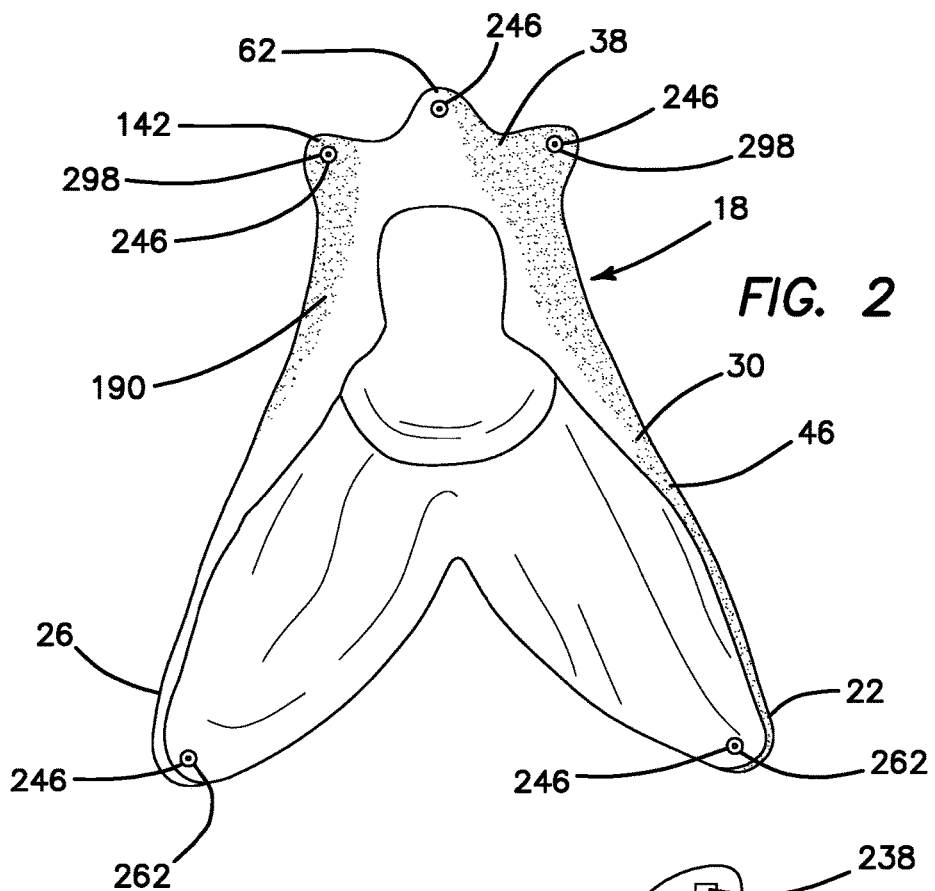
FIG. 2 is a plan view of the pillow cover illustrating the elongated star-point shaped extensions, their point attachment devices and accessory fastening devices.
Figure 3:
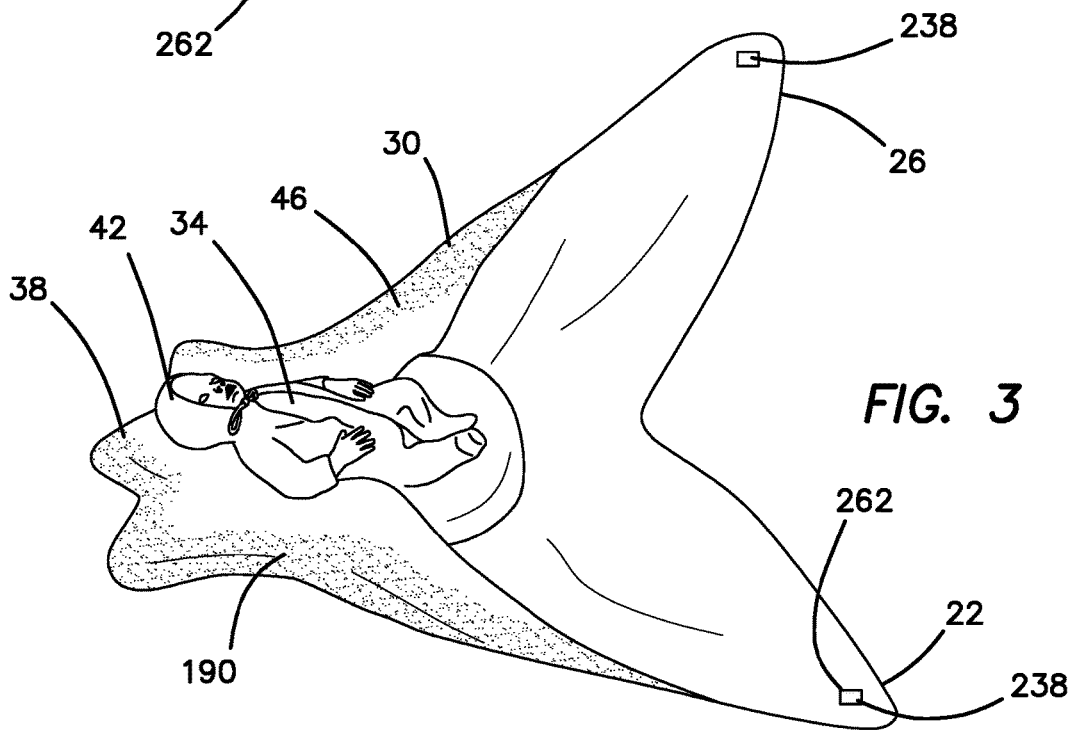
FIG. 3 is a perspective view of a baby disposed on the baby handling device prior to fastening the elongated star-point shaped extensions.
Figure 9:
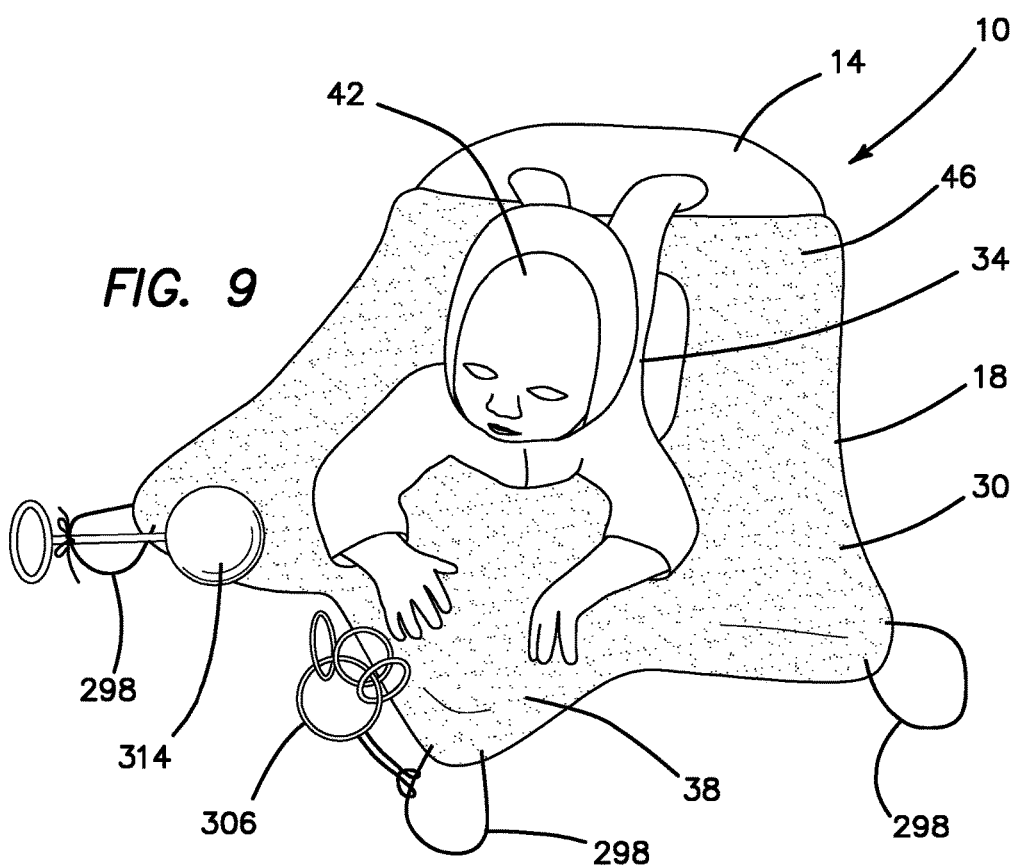
FIG. 9 is a perspective view of a baby disposed prone on the baby handling device illustrating accessory fastening devices, toys and accessories.
Figure 10:
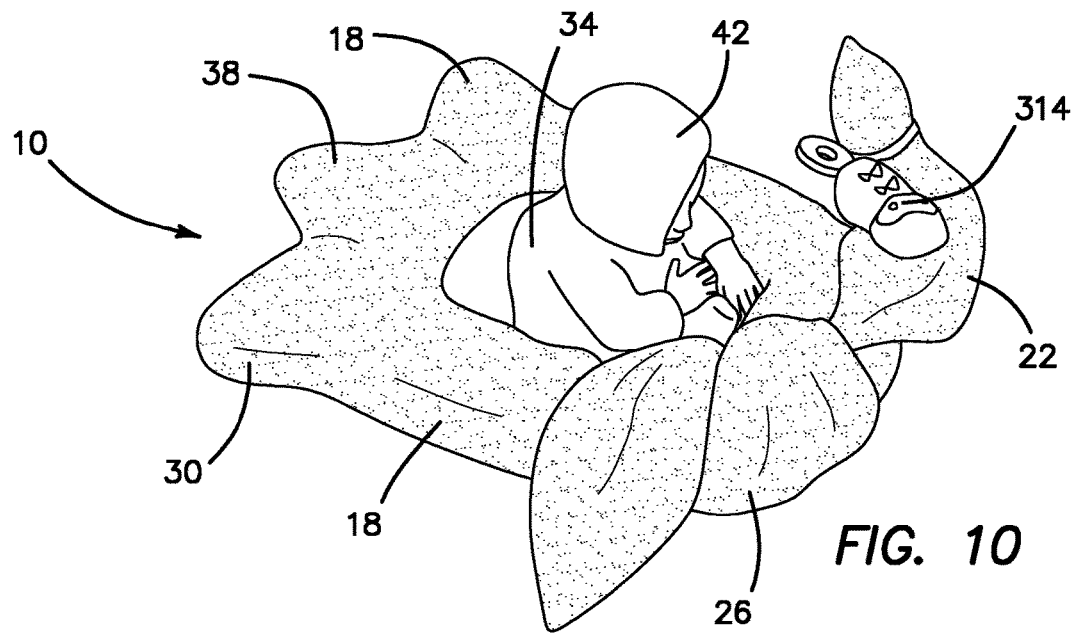
FIG. 10 is a perspective view of a baby disposed on the baby handling device in a sitting position illustrating the elongated star-point shaped extensions tied to secure the baby's feet.
Figure 11:
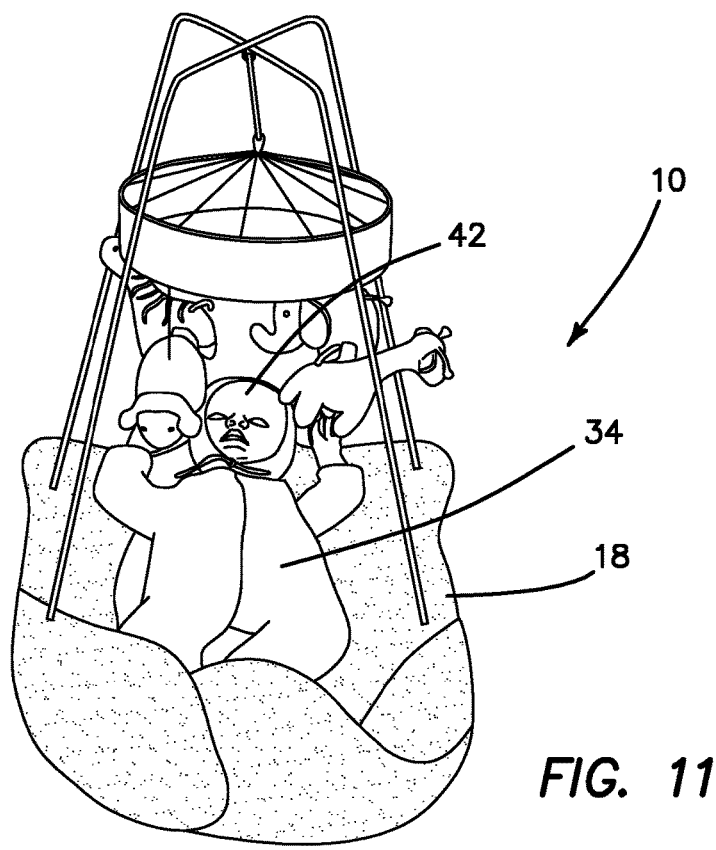
FIG. 11 is a perspective view of a baby disposed supine on the baby handling device illustrating a suspended toy holder positioned on the device above the baby.

(17) In yet another variant, as illustrated in FIGS. 2, 9 and 10, at least one accessory fastening device 298 is provided. The accessory fastening device 298 is attached to the cover 18 where the cover 18 extends over any of the central point-shaped portion 62 and the first 142 and second 146 point-shaped portions of the irregular star-shaped pillow 14, the accessory fastening device 298 providing an attachment point 302 for toys 306, pacifiers 310 and other accessories 314.

Figure 1E:
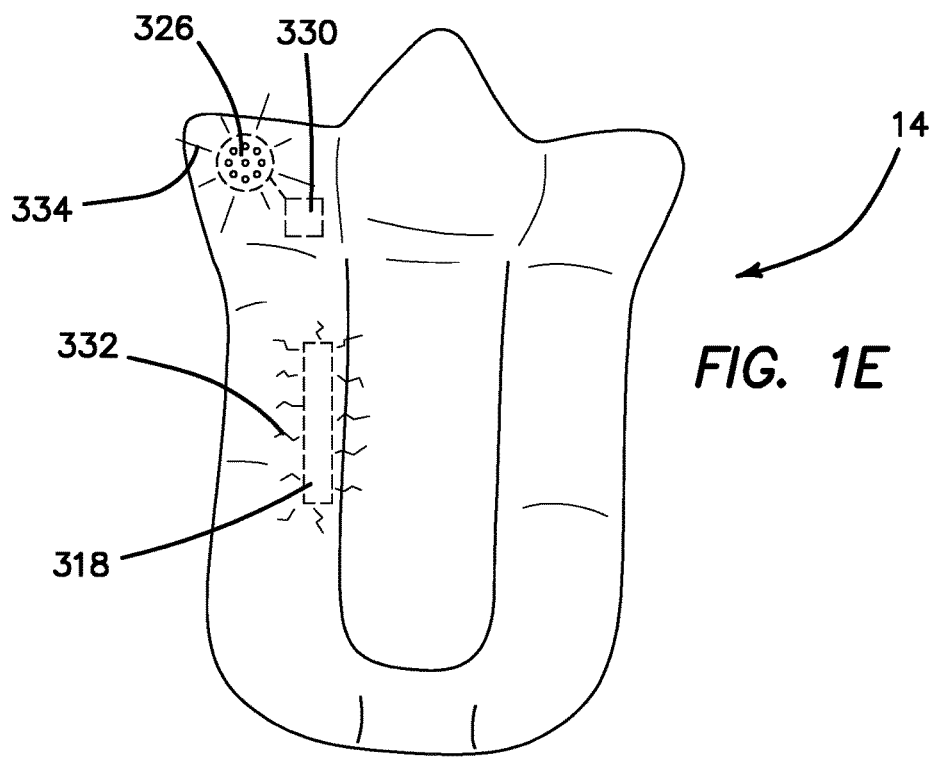
FIG. 1E is a plan view of the pillow of the FIG. 1 embodiment illustrating a speaker, sound source and vibrating element.

(18) In a further variant, as illustrated in FIG. 1E, the irregular star-shaped pillow 14 further includes an electrically operated vibrating element 318. The element 318 causes the device 10 to provide a soothing vibration 322 to induce sleep in the baby 34.

(19) In still a further variant, the irregular star-shaped pillow 14 further includes at least one loudspeaker 326 and electrically operated sound source 330. The sound source 330 provides music 334 to provide a calming environment for the baby 34.

Figure 16:
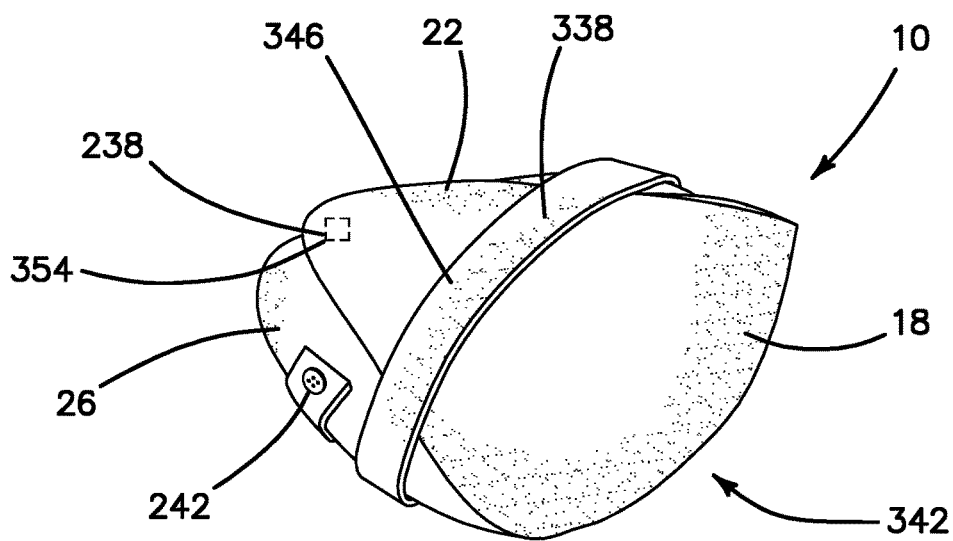
FIG. 16 is a perspective view of the baby handling device secured as a compact bundle with the combination fastening and carrying strap.

(20) In yet a further variant, as illustrated in FIG. 16, a combination fastening and carrying strap 338 is provided. The strap 338 serves to hold the device 10 in a compact bundle 342 and to provide a carrying handle 346. The strap 338 is attached to the removable cover 18 with any of stitching 350, hook and eye combinations (not shown), buttons 242, snaps 246, looping and hooking fasteners 238 and zippers 250.

(21) In another variant of the invention, as illustrated in FIG. 16, the removable cover includes a plurality of attachment devices 354. The attachment devices 354 secure the elongated star-point shaped extensions 22, 26 about the irregular star-shaped pillow 14 in a compact bundle 342.

Figure 15:
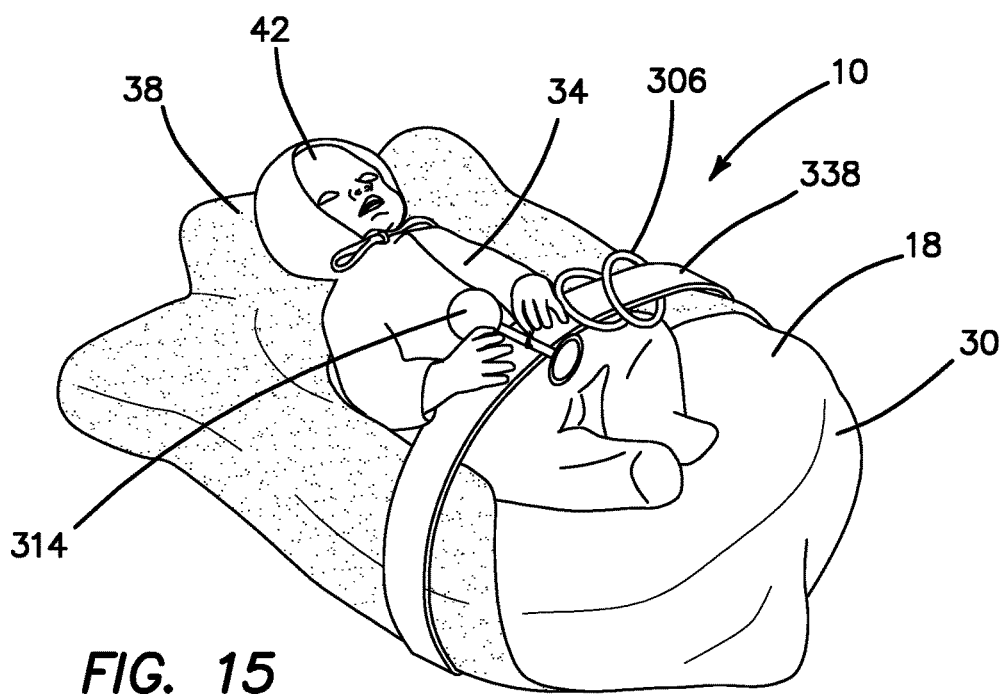
FIG. 15 is a perspective view of a baby disposed supine on the baby handling device illustrating combination fastening and carrying strap with attached toys and accessories.

(22) In still another variant, as illustrated in FIG. 15, the combination fastening and carrying strap 338 provides a mounting for baby toys 306 and accessories 314 and is adapted to secure the baby 34 to the irregular star-shaped pillow 14.

(23) In yet another variant, as illustrated in FIGS. 12-14, the elongated star-point shaped extension 22, 26 of the cover 18 is adapted to provide a privacy shield 358 during nursing.

Figure 18:
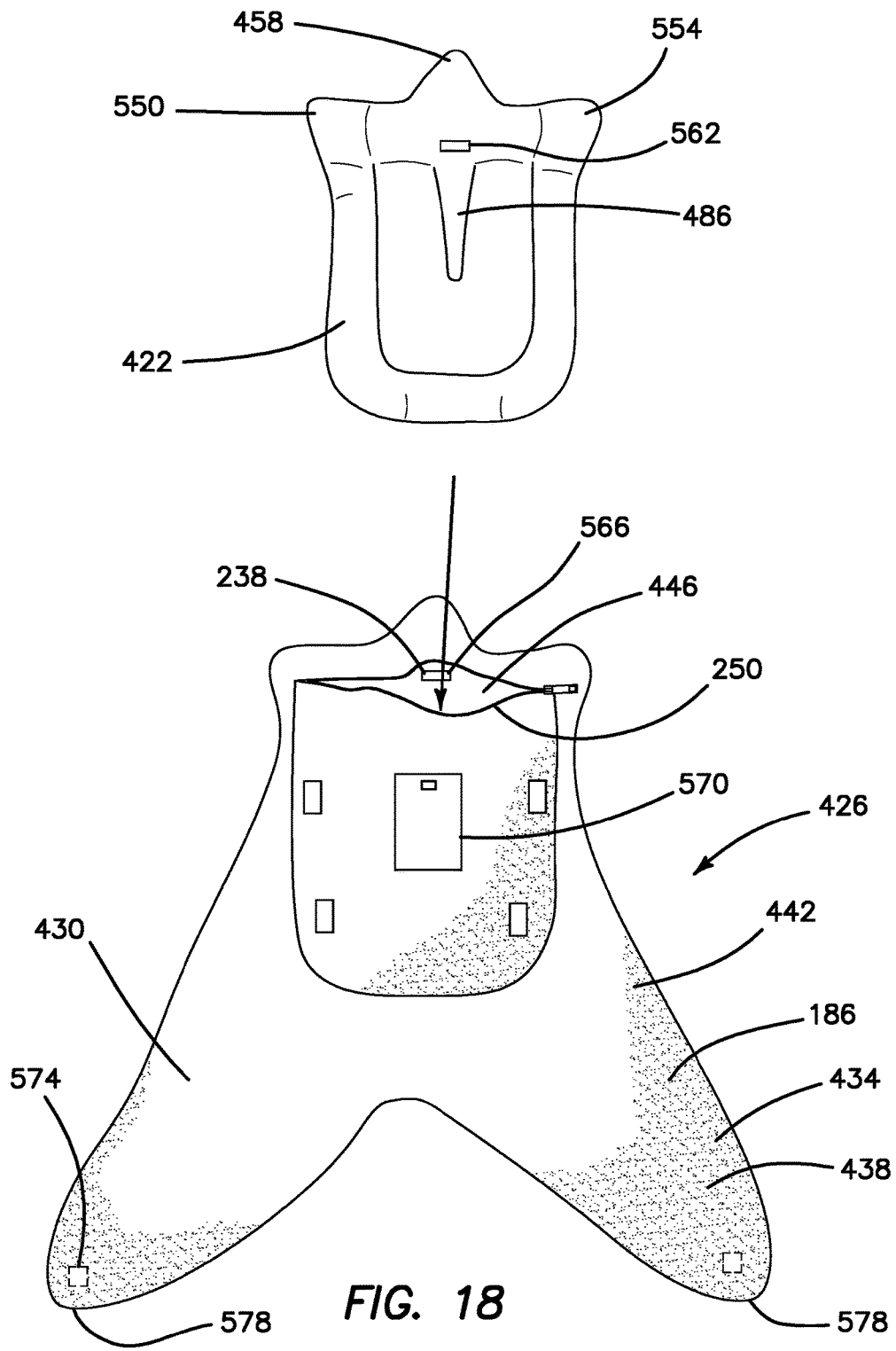
FIG. 18 is a plan view of a two baby embodiment of the invention illustrating the center arm rest of the pillow.

(24) In a further variant, as illustrated in FIG. 18, a carrying bag 362 is provided. The bag 362 is sized and shaped to enclose any of the removable, washable pillow cover 18, the irregular star-shaped pillow 14 and baby supplies 366.

(25) In still a further variant, a carrying strap 370 is provided.

(26) In yet a further variant, the carrying bag 362 further includes at least one pocket 374.

Figure 1F:
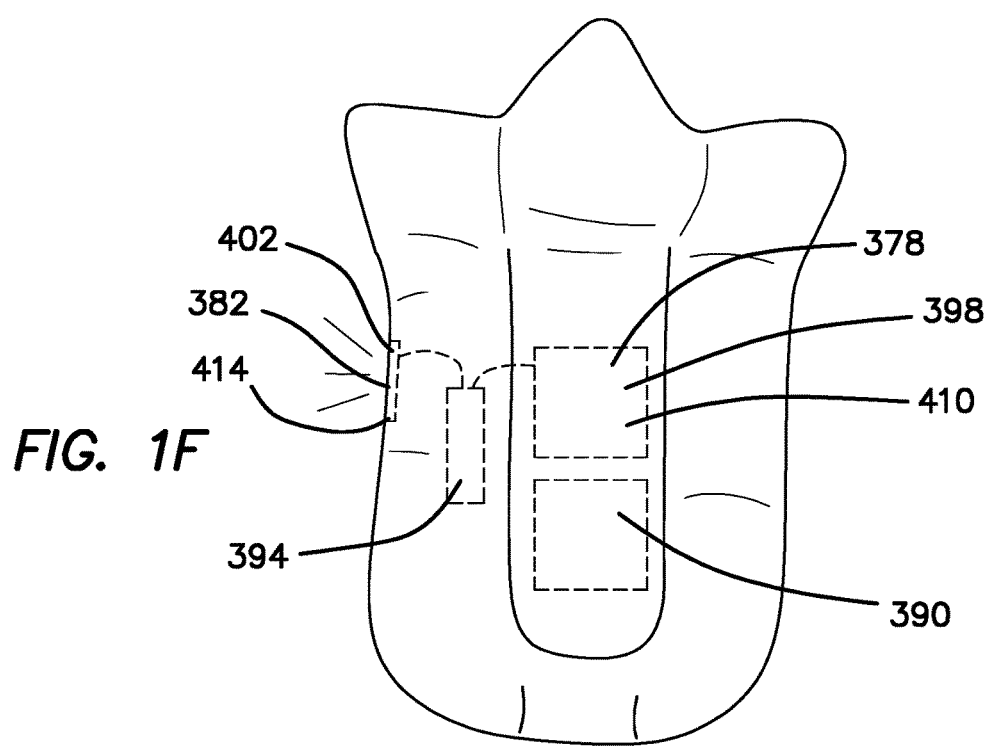
FIG. 1F is a plan view of the pillow of the FIG. 1 embodiment illustrating a heartbeat, respiration or motion monitor, weight sensor, alarm system and battery life indicator.

(27) In another variant of the invention, as illustrated in FIG. 1F, a heartbeat monitoring system 378 is provided. The heartbeat monitoring system 378 further includes an alarm system 382 to indicate absence of a baby's heartbeat (not shown).

(28) In still another variant, the irregular star-shaped pillow 14 further includes a weight sensing system 390 to determine if the baby 34 is positioned upon the pillow 14 and the heartbeat monitoring system 378 should be activated.

(29) In yet another variant, a battery life indicator 394 is provided. The battery life indicator 394 confirms that the heartbeat monitoring system 378 will receive sufficient power for a predetermined period of time once the weight sensing system 390 determines that the baby 34 is disposed upon the pillow 14.

(30) In still another variant, the irregular star-shaped pillow further includes a respiration monitoring system 398. The respiration monitoring system 398 further includes an alarm system 402 to indicate absence of a baby's breathing (not shown).

(31) In yet another variant, the irregular star-shaped pillow 14 further includes a weight sensing system 390 to determine if the baby 34 is positioned upon the pillow 14 and the respiration monitoring system 398 should be activated.

(32) In a further variant, a battery life indicator 394 is provided. The battery life indicator 394 confirms that the respiration monitoring system 398 will receive sufficient power for a predetermined period of time once the weight sensing system 390 determines that the baby 34 is disposed upon the pillow 14.

(33) In still a further variant, the irregular star-shaped pillow further includes a motion detection system 410. The motion detection system 410 further includes an alarm system 414 to indicate absence of a baby's movement (not shown).

(34) In yet a further variant, the irregular star-shaped pillow 14 further includes a weight sensing system 390 to determine if the baby 34 is positioned upon the pillow 14 and the motion detection system 410 should be activated.

(35) In still a further variant, a battery life indicator 394 is provided. The battery life indicator 394 confirms that the motion detection system 410 will receive sufficient power for a predetermined period of time once the weight sensing system 390 determines that the baby 34 is disposed upon the pillow 14.

(36) In yet a further variant, as illustrated in FIGS. 18-23, an irregular star-shaped pillow 422 is provided. A removable, washable pillow cover 426 is provided. The cover 426 is sized and shaped to fit over and extend from the irregular star-shaped pillow 422 and provides at least two elongated star-point shaped extensions 430, 434. The extensions 430, 434 are formed of flexible material 438 and adapted to fold over and enclose at least a portion of two babies 34 positioned on the cover 426. An upper portion of the cover 426 is adapted to support and control movement of the babies' heads 42 when the elongated star-point shaped extensions 430, 434 are wrapped around the babies 34 and fastened to an outer surface 442 of the cover 426. The cover 426 has a closeable opening 446 sized and shaped to permit insertion and removal of the pillow 422.

Figure 24:
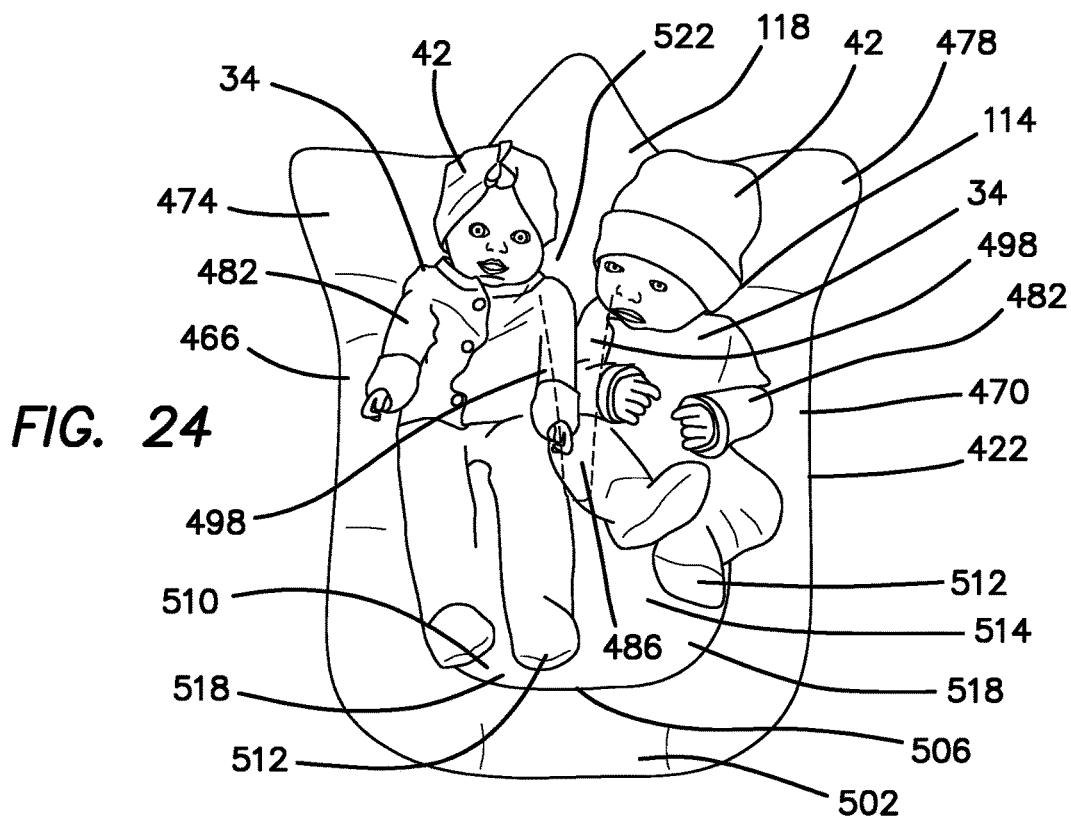
FIG. 24 is a plan view of the two baby embodiment of the pillow illustrating the center arm rest, lower pillow section, foot stop and first and second side sections.
Figure 25:
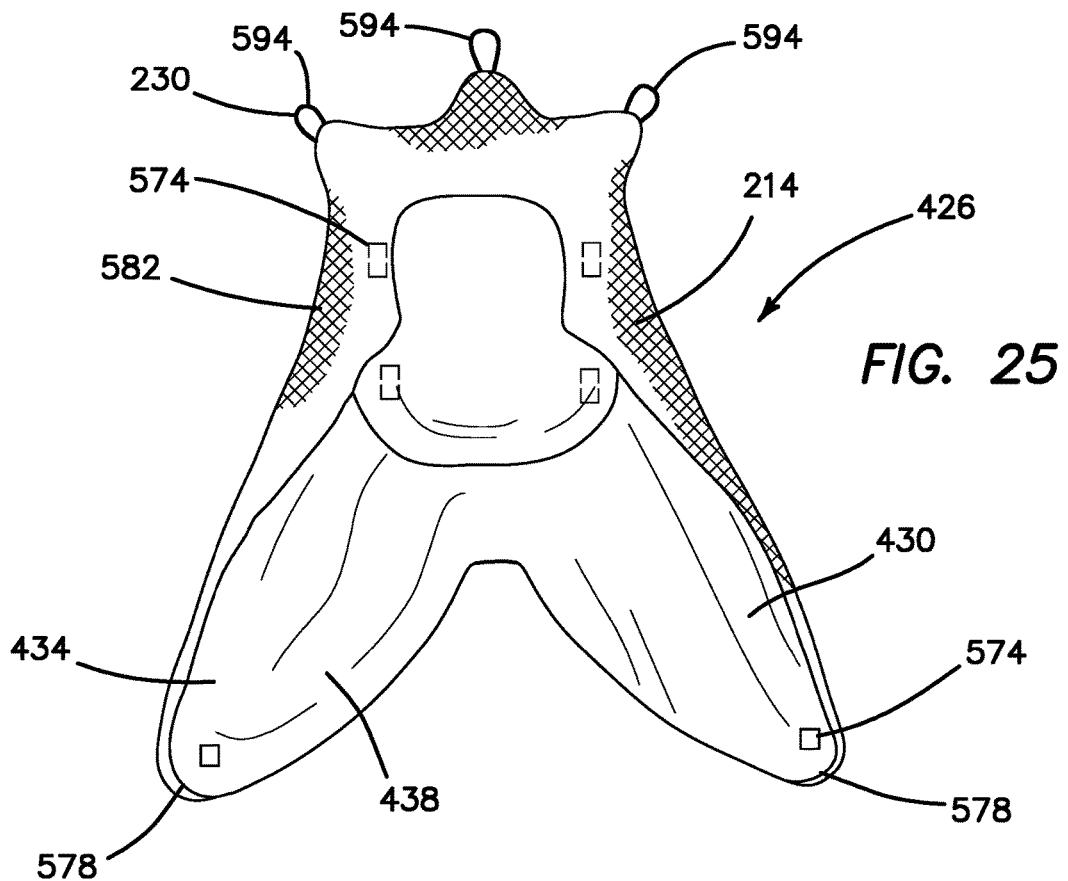
FIG. 25 is a plan view of the two baby embodiment of the pillow cover illustrating point attachment devices for the elongated star-point shaped extensions and accessory fastening devices.
Figure 26:
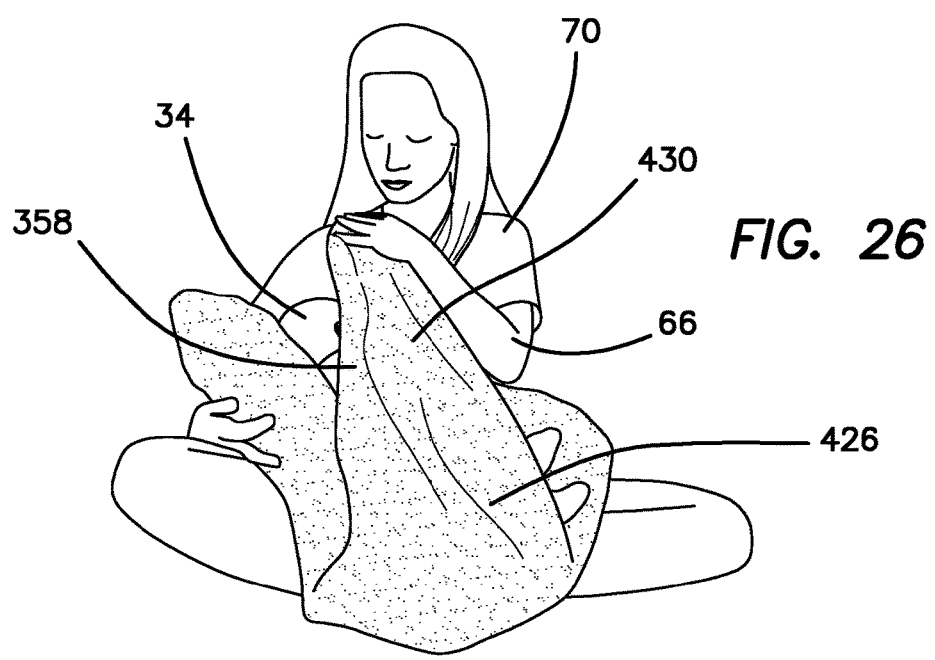
FIG. 26 is a perspective view of the two baby embodiment of the baby handling device being used by a nursing mother as a support for a baby and as a privacy shield.

(37) In another variant of the invention, as illustrated in FIGS. 24-26, the irregular star-shaped pillow 422 is formed of resilient material 450 and further includes a broad upper section 454 sized and shaped to support the babies' heads 42. A central point-shaped portion 458 extends upwardly from a center point 462 of the upper section 454. The point-shaped portion 458 is adapted to lodge under an arm 66 of a breast feeding mother 70. First 466 and second 470 side sections are provided. The side sections 466, 470 are joined to first 474 and second 478 ends of the upper section 454 and are sized and shaped to support outer arms 482 of the babies 34. A center arm rest 486 is provided. The center arm rest 486 is joined to a center point 490 of a bottom edge 494 of the upper section 454 and is sized and shaped to support inner arms 498 of the babies 34. A lower section 502 is provided. The lower section 502 is joined to the first 466 and second 470 side sections and is sized and shaped to provide a stop 506 for the babies' feet 512. The stop 506 prevents the babies 34 from sliding downwardly from center sections 510, 514. The broad upper section 454, the side sections 466, 470, the center arm rest 486 and the lower section 502 surround the first 510 and second 514 center sections. The center sections 510, 514 provide support platforms 518 for the babies 34 and work with the broad upper section 454 to control an inclination 114 of the babies' heads 42 when the babies 34 are disposed on their backs 118 upon the pillow 422.

(38) In still another variant, as illustrated in FIGS. 21 and 22, the irregular star-shaped pillow 422 further includes first 522, second 526, third 530 and fourth 534 dividers. The dividers 522, 526, 530, 534 are located on either side of a center point 462 of the upper section 454 and serve to control positioning of the babies' heads 42 on the upper section 454.

Figure 23:
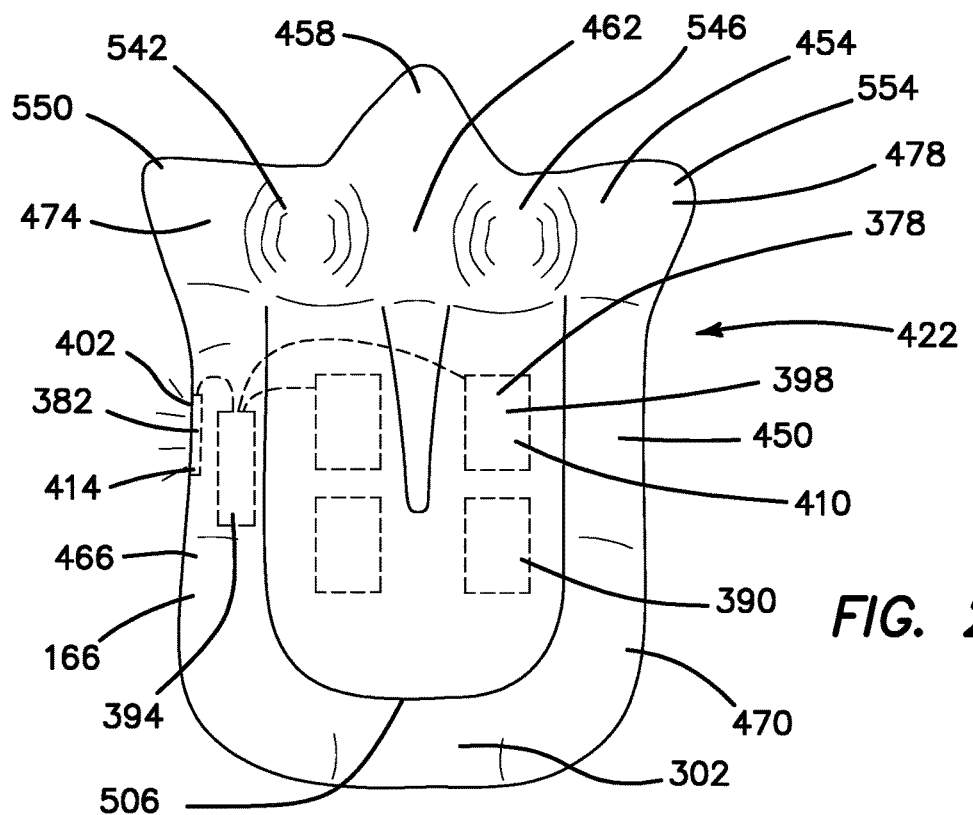
FIG. 23 is a plan view of a two baby embodiment of the pillow illustrating a heartbeat, respiration or motion monitor, weight sensor, alarm system and battery life indicator and first and second depressions for the heads of the babies.

(39) In yet another variant, as illustrated in FIGS. 23 and 24, the irregular star-shaped pillow 422 further includes first 542 and second 546 depressions. The first 542 and second 546 depressions are disposed on either side of a center point 462 of the upper section 454 and serve to control positions of the babies' heads 42 on the upper section 454 to limit inclination 114 of the babies' heads 42.

(40) In a further variant, the irregular star-shaped pillow 422 further includes first 550 and second 554 point-shaped portions. The first 550 and second 554 point-shaped portions extend outwardly from the first 474 and second 478 ends of the upper section 454.

Figure 30:
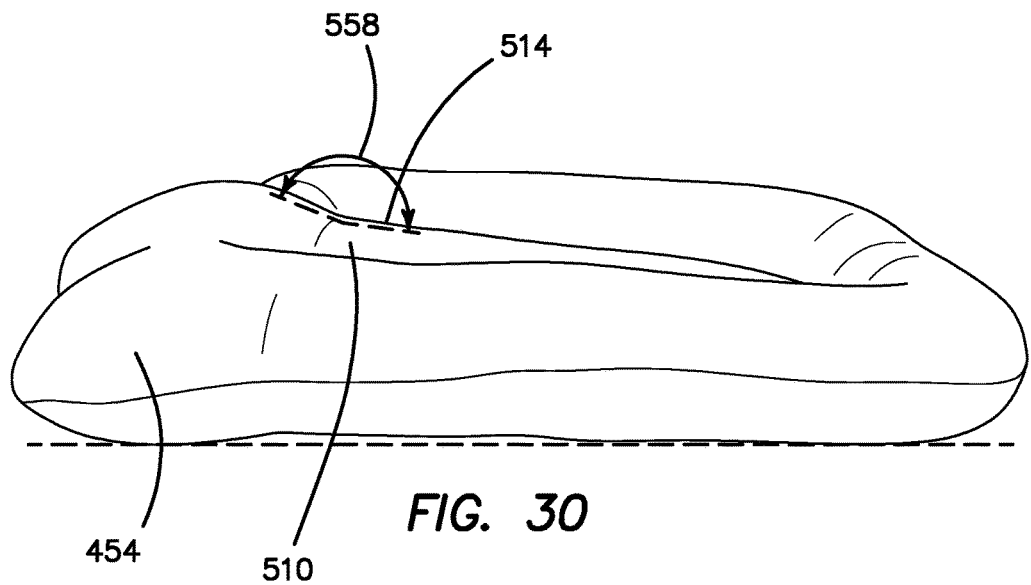
FIG. 30 is a perspective view of the two baby embodiment of the pillow illustrating the minimum included angle between the upper section and either of the first and second center sections.

(41) In still a further variant, as illustrated in FIG. 30, an included angle 558 formed between the broad upper section 454 and either of the first 510 and second 514 center sections is greater than or equal to 150 degrees.

Figure 19:
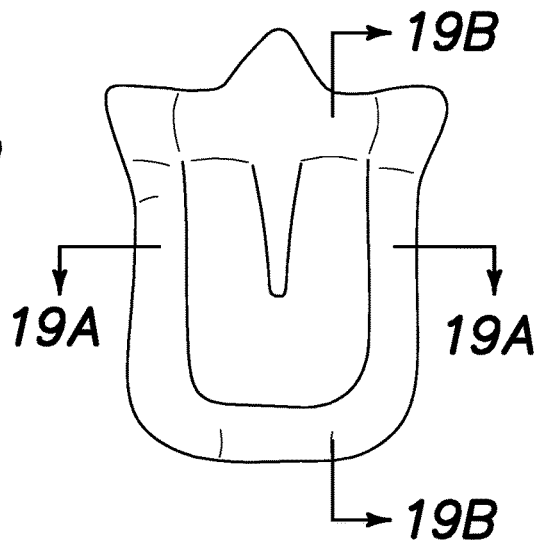
FIG. 19 is a plan view of a two baby embodiment of the pillow.
Figure 19A:
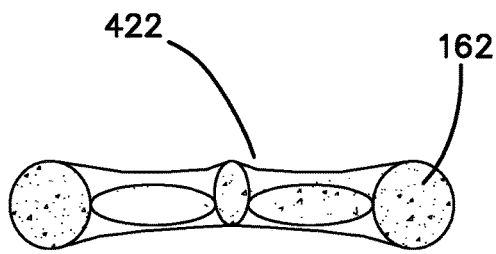
FIG. 19A is a cross-sectional view of the FIG. 19 embodiment taken along the line 19A-19A, illustrating the cotton batting core.
Figure 19B:
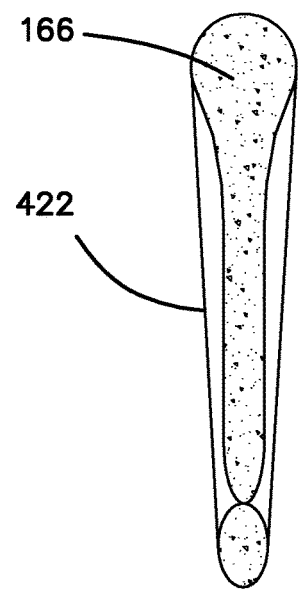
FIG. 19B is a cross-sectional view of the FIG. 19 embodiment taken along the line 19B-19B, illustrating the polyester batting core.
Figure 20:
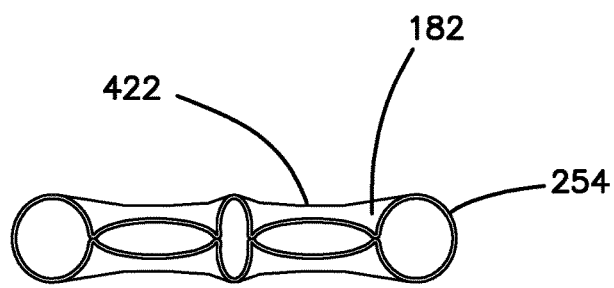
FIG. 20 is a cross-sectional view of the pillow formed as an inflatable bladder.

(42) In yet a further variant, as illustrated in FIGS. 19-20 the resilient material 450 is selected from the group that includes cotton batting 162, polyester batting 166, foam rubber 170, memory foam 174, memory foam segments (not shown) and an inflatable bladder 182.

(43) In another variant of the invention, as illustrated in FIG. 18, the removable, washable pillow cover 426 is formed of material selected from the group includes terrycloth 186, cotton (not shown), polyester (not shown), cotton-polyester blends (not shown), wool (not shown), rayon (not shown), bamboo (not shown), satin weave fabrics (not shown) and sateen weave fabrics 218.

(44) In still another variant, the irregular star-shaped pillow 422 further includes at least one fastening device 562. The cover 426 includes at least one mating fastening device 566 for securing the pillow 422 within the cover 426.

(45) In yet another variant, the fastening device 562 is selected from the group that Includes tie strings (not shown), hook and eye combinations (not shown), hooking and looping devices 238, buttons 242, snaps (not shown) and zippers 250.

(46) In a further variant, as illustrated in FIG. 20, the irregular star-shaped pillow 422 is formed of impermeable material 254.

(47) In still a further variant, as illustrated in FIG. 18, the removable cover 426 further includes a storage pocket 570.

Figure 27:
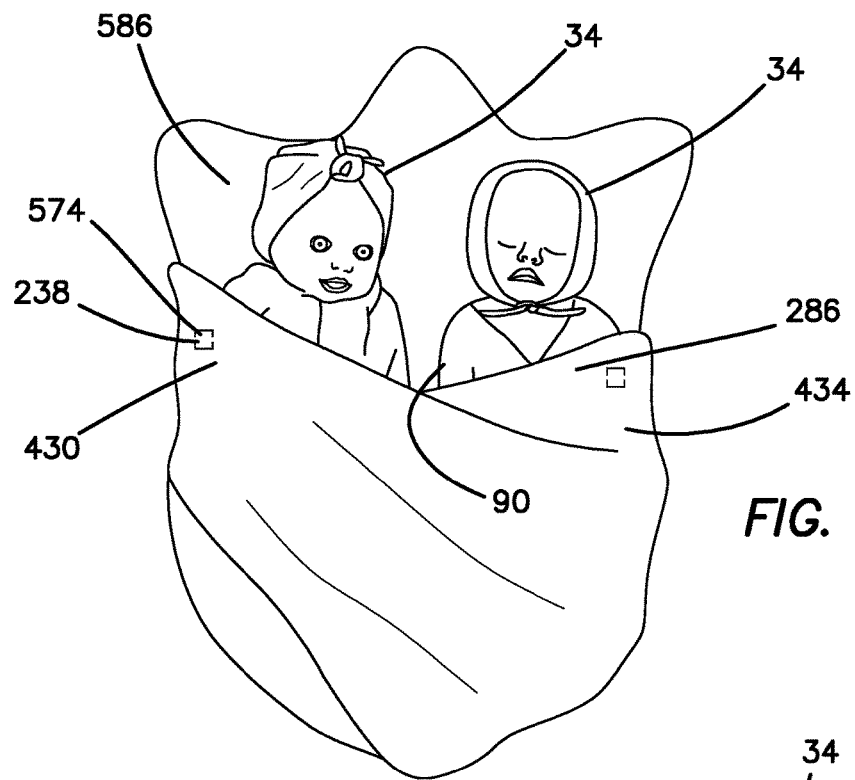
FIG. 27 is a plan view of the two baby embodiment of the baby handling device illustrating the babies with their arms secured and the elongated star-point shaped extensions in a first position.
Figure 28:
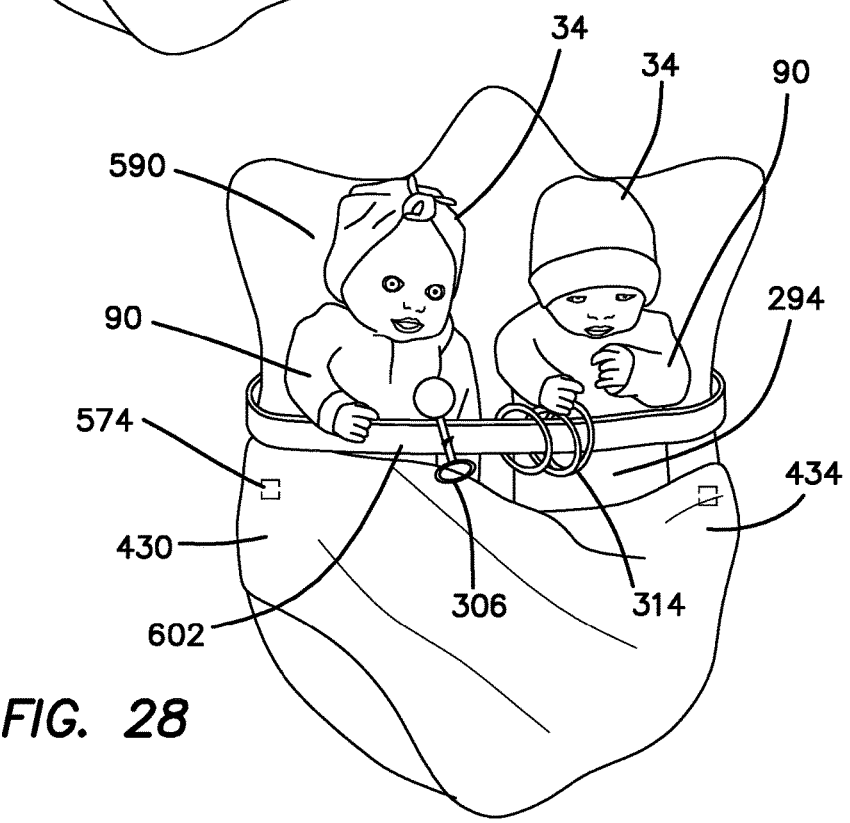
FIG. 28 is a plan view of the two baby embodiment of the baby handling device illustrating the babies with their arms unsecured and the elongated star-point shaped extensions in a second position.

(48) In yet a further variant, as illustrated in FIGS. 25, 27 and 28, at least one point attachment device 574 is provided. The point attachment device 574 provides attachment for a distal end 578 of the elongated star-point shaped extension 430, 434 to at least one location 580 on an exterior surface 582 of the cover 426, thereby adapting the extension 430, 434 to secure the babies 34 in predetermined positions 586.

(49) In another variant of the invention, the point attachment device 574 in selected from the group includes tie strings 230, hook and eye combinations (not shown), hooking and looping devices 238, buttons (not shown), snaps (not shown) and zippers 250.

(50) In still another variant, as illustrated in FIG. 27, the point attachment device 574 is disposed to secure the babies 34 in a first position 586. The first position 586 attaches the extension 430, 434 at shoulder height 286 for the babies 34. The first position 586 constrains the arms 90 of the babies 34.

(51) In yet another variant, as illustrated in FIG. 28, the point attachment device 574 is disposed to secure the babies 34 in a second position 590. The second position 590 attaches the extension 430, 434 at abdomen height 294 for the babies 34. The second position 590 permits movement of the arms 90 of the babies 34.

(52) In a further variant, as illustrated in FIGS. 23 and 25, at least one accessory fastening device 594 is provided. The accessory fastening device 594 is attached to the cover 426 where the cover 426 extends over any of the central point-shaped portion 458 and the first 550 and second 554 point-shaped portions of the irregular star-shaped pillow 422. The accessory fastening device 594 provides an attachment point 598 for toys 306, pacifiers 310 and other accessories 314.

(53) In still a further variant, as illustrated in FIG. 22, the irregular star-shaped pillow 422 further includes an electrically operated vibrating element 318. The element 318 causes the device 10 to provide a soothing vibration 322 to induce sleep in the babies 34.

(54) In yet a further variant, the irregular star-shaped pillow 422 further includes at least one loudspeaker 326 and electrically operated sound source 330. The sound source 330 provides music 334 to provide a calming environment for the babies 34.

Figure 29:
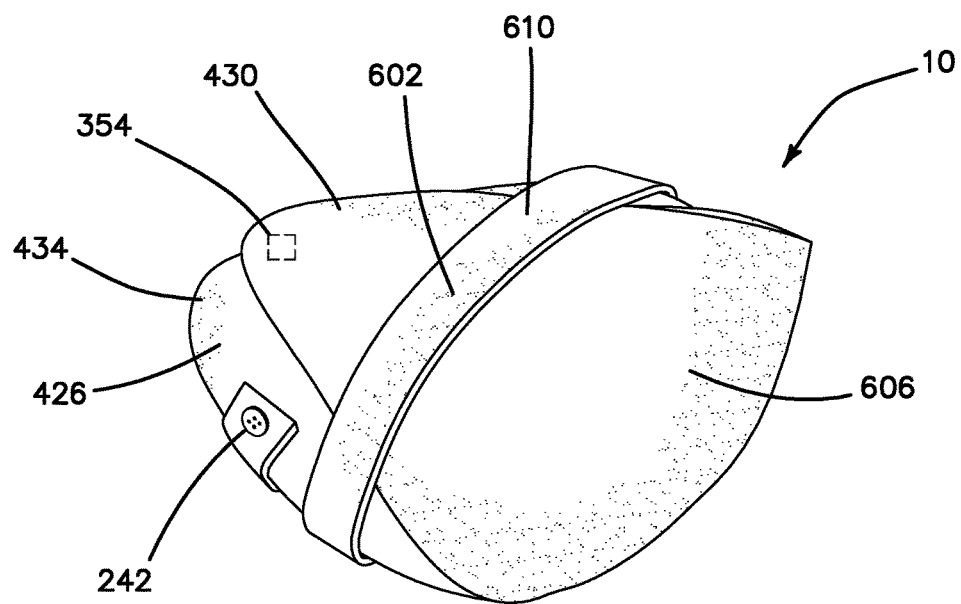
FIG. 29 is a perspective view of the two baby embodiment of the baby handling device configured as a compact bundle with the combination fastening and carrying strap.

(55) In another variant of the invention, as illustrated in FIG. 29, a combination fastening and carrying strap 602 is provided. The strap 602 serves to hold the device 10 in a compact bundle 606 and to provide a carrying handle 610. The strap 602 is attached to the removable cover 426 with any of stitching (not shown), hook and eye combinations (not shown), buttons 242, snaps (not shown), looping and hooking fasteners 238 and zippers 250.

(56) In still another variant, the removable cover 426 includes a plurality of attachment devices 354. The attachment devices 354 secure the elongated star-point shaped extensions 430, 434 about the irregular star-shaped pillow 422 in a compact bundle 606.

(57) In yet another variant, as illustrated in FIG. 28, the combination fastening and carrying strap 602 provides a mounting for baby toys 306 and accessories 314 and is adapted to secure the babies 34 to the irregular star-shaped pillow 422.

(58) In a further variant, as illustrated in FIG. 26 the elongated star-point shaped extension 430, 434 of the cover 426 is adapted to provide a privacy shield 358 during nursing.

Figure 17:
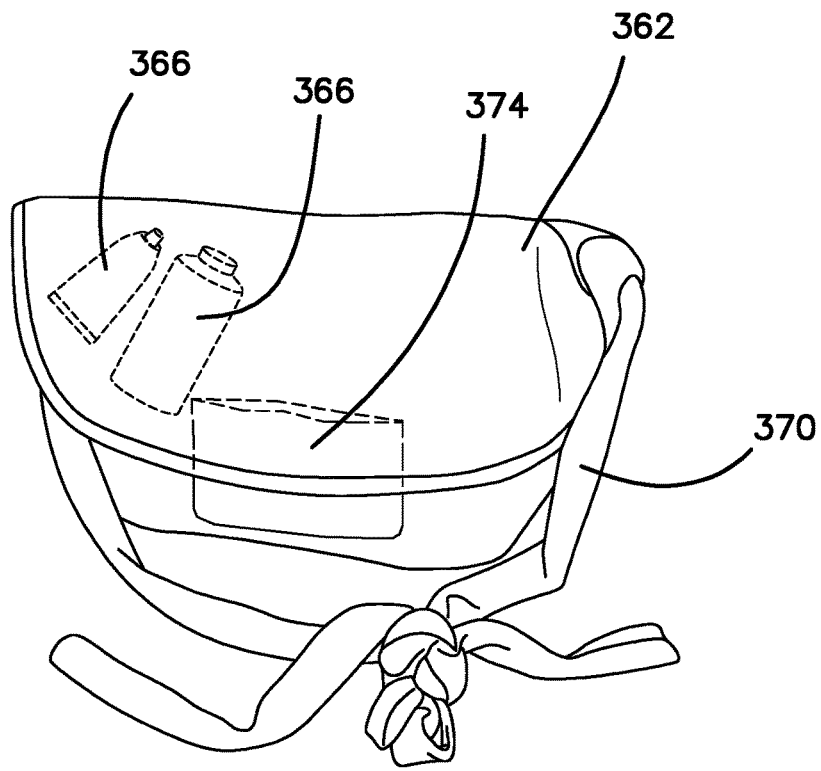
FIG. 17 is a perspective view of the carrying bag for the baby handling device.

(59) In still a further variant, as illustrated in FIG. 17, a carrying bag 362 is provided. The bag 362 is sized and shaped to enclose any of the removable, washable pillow cover 426, the irregular star-shaped pillow 422 and baby supplies 366.

(60) In yet a further variant, a carrying strap 370 is provided.

(61) In another variant of the invention, the carrying bag 362 further includes at least one pocket 374.

(62) In still another variant, the irregular star-shaped pillow 422 further includes a heartbeat monitoring system 378. The heartbeat monitoring system 378 further includes an alarm system 382 to indicate absence of either of the babies' heartbeats (not shown).

(63) In yet another variant, the irregular star-shaped pillow 422 further includes a weight sensing system 390 to determine if either of the babies 34 is positioned upon the pillow 422 and the heartbeat monitoring system 378 should be activated.

(64) In a further variant, a battery life indicator 394 is provided. The battery life indicator 394 confirms that the heartbeat monitoring system 378 will receive sufficient power for a predetermined period of time once the weight sensing system 390 determines that either of the babies 34 is disposed upon the pillow 422.

(65) In still a further variant, the irregular star-shaped pillow 422 further includes a respiration monitoring system 398. The respiration monitoring system 398 further includes an alarm system 402 to indicate absence of either of the babies' breathing (not shown).

(66) In yet a further variant, the irregular star-shaped pillow 422 further includes a weight sensing system 390 to determine if either of the babies 34 is positioned upon the pillow 422 and the respiration monitoring system 398 should be activated.

(67) In another variant of the invention, a battery life indicator 394 is provided. The battery life indicator 394 confirms that the respiration monitoring system 398 will receive sufficient power for a predetermined period of time once the weight sensing system 390 determines that either of the babies 34 is disposed upon the pillow 422.

(68) In still another variant, the irregular star-shaped pillow 422 further includes a motion detection system 410. The motion detection system 410 further includes an alarm system 414 to indicate absence of either of the babies' movement (not shown).

(69) In yet another variant, the irregular star-shaped pillow 422 further includes a weight sensing system 390 to determine if either of the babies 34 is positioned upon the pillow 422 and the motion detection system 410 should be activated.

(70) In a final variant of the invention, a battery life indicator 394 is provided. The battery life indicator 394 confirms that the motion detection system 410 will receive sufficient power for a predetermined period of time once the weight sensing system 390 determines that either of the babies 34 is disposed upon the pillow 422.

The invention claimed is:

1. A baby handling device, comprising:
 an irregular star-shaped pillow;
 a removable, washable pillow cover, said cover being sized and shaped to fit over and extend from said irregular star-shaped pillow and providing at least two elongated star-point shaped extensions, said extensions being formed of flexible material and adapted to fold over and enclose at least a portion of a baby positioned on said cover;
 an upper portion of said cover adapted to support and control movement of said baby's head when said elongated star-point shaped extensions are wrapped around said baby and fastened to an outer surface of said cover; and
 said cover having a closeable opening sized and shaped to permit insertion and removal of said pillow.

2. The baby handling device, as described in claim 1, wherein said irregular star-shaped pillow is formed of resilient material and further comprises:
 a broad upper section sized and shaped to support said baby's head;
 a central point-shaped portion extending upwardly from a center point of said upper section, said central point-shaped portion adapted to lodge under an arm of a breast feeding mother;
 first and second side sections, said side sections being joined to first and second ends of said upper section and being sized and shaped to support said baby's arms;
 a lower section, said lower section being joined to said first and second side sections and being sized and shaped to provide a stop for said baby's feet, said stop preventing said baby from sliding downwardly from a center section;
 said broad upper section, said side sections and said lower section surrounding said center section, said center section providing a support platform for said baby and working with said broad upper section to control an inclination of said baby's head when said baby is on its back and disposed upon said pillow.

3. The baby handling device, as described in claim 2, wherein said irregular star-shaped pillow further comprises first and second dividers, said dividers being disposed on either side of said center point of said upper section and serving to urge said baby's head toward said center point, said pillow having a reduced amount of stuffing between said dividers.

4. The baby handling device, as described in claim 2, wherein said irregular star-shaped pillow further comprises a central depression, said central depression being disposed at said center point of said upper section and serving to control a position of said baby's head on said upper section and to limit inclination of said baby's head.

5. The baby handling device, as described in claim 2, wherein said irregular star-shaped pillow further comprises first and second point-shaped portions, said first and second point-shaped portions extending outwardly from said first and second ends of said upper section.

6. The baby handling device, as described in claim 2, wherein an included angle formed between said broad upper section and said center section is greater than or equal to 150 degrees.

7. The baby handling device, as described in claim 2, wherein said resilient material is selected from the group comprising:
 cotton batting, polyester batting, foam rubber, memory foam, memory foam segments and an inflatable bladder.

8. The baby handling device, as described in claim 1, wherein said removable, washable pillow cover is formed of material selected from the group comprising:
terrycloth, cotton, polyester, cotton-polyester blends, wool, rayon, bamboo, satin weave fabrics and sateen weave fabrics.

9. The baby handling device, as described in claim 2, wherein said irregular star-shaped pillow further comprises at least one fastening device and said cover comprises at least one mating fastening device for securing said pillow within said cover.

10. The baby handling device, as described in claim 9, wherein said at least one fastening device is selected from the group comprising:
tie strings, hook and eye combinations, hooking and looping devices, buttons, snaps and zippers.

11. The baby handling device, as described in claim 2, wherein said irregular star-shaped pillow is formed of impermeable material.

12. The baby handling device, as described in claim 1, wherein said removable cover further includes a storage pocket.

13. The baby handling device, as described in claim 1, further comprising at least one point attachment device, said at least one point attachment device providing attachment for a distal end of each of said elongated star-point shaped extensions to at least one location on an exterior surface of said cover, thereby adapting said extensions to secure said baby in a predetermined position.

14. The baby handling device, as described in claim 13, wherein said at least one point attachment device in selected from the group comprising:
tie strings, hook and eye combinations, hooking and looping devices, buttons, snaps and zippers.

15. The baby handling device, as described in claim 13, wherein said at least one point attachment device is disposed to secure said baby in a first position, said first position attaching said extension at shoulder height for said baby, said first position constraining arms of said baby.

16. The baby handling device, as described in claim 13, wherein said at least one point attachment device is disposed to secure said baby in a second position, said second position attaching said extension at abdomen height for said baby, said second position permitting movement of arms of said baby.

17. The baby handling device, as described in claim 5, further comprising at least one accessory fastening device, said at least one accessory fastening device being attached to said cover where said cover extends over any of said central point-shaped portion and said first and second point-shaped portions of said irregular star-shaped pillow, said at least one accessory fastening device providing an attachment point for toys, pacifiers and other accessories.

18. The baby handling device, as described in claim 1, wherein said irregular star-shaped pillow further comprises an electrically operated vibrating element, said element causing said device to provide a soothing vibration to induce sleep in said baby.

19. The baby handling device, as described in claim 1, wherein said irregular star-shaped pillow further comprises at least one loudspeaker and electrically operated sound source, said sound source providing music to provide a calming environment for said baby.

20. The baby handling device, as described in claim 1, further comprising a combination fastening and carrying strap, said strap serving to hold the device in a compact bundle and to provide a carrying handle, said strap being attached to said removable cover with any of stitching, hook and eye combinations, buttons, snaps, looping and hooking fasteners and zippers.

21. The baby handling device, as described in claim 1, wherein said removable cover comprises a plurality of attachment devices, said attachment devices securing said elongated star-point shaped extensions about said irregular star-shaped pillow in a compact bundle.

22. The baby handling device, as described in claim 20, wherein said combination fastening and carrying strap provides a mounting for baby toys and accessories and is adapted to secure said baby to the irregular star-shaped pillow.

23. The baby handling device, as described in claim 1, wherein each of said elongated star-point shaped extensions of said cover is adapted to provide a privacy shield during nursing.

24. The baby handling device, as described in claim 2, further comprising a carrying bag, said bag being sized and shaped to enclose any of said removable, washable pillow cover, said irregular star-shaped pillow and baby supplies.

25. The baby handling device, as described in claim 20, further comprising attachments for a carrying strap.

26. The baby handling device, as described in claim 24, wherein said carrying bag further comprises at least one pocket.

27. The baby handling device, as described in claim 1, wherein said irregular star-shaped pillow further comprises a heartbeat monitoring system, said heartbeat monitoring system further comprising an alarm system to indicate absence of said baby's heartbeat.

28. The baby handling device, as described in claim 27, wherein said irregular star-shaped pillow further comprises a weight sensing system to determine if said baby is positioned upon said pillow and said heartbeat monitoring system should be activated.

29. The baby handling device, as described in claim 28, further comprising a battery life indicator, said battery life indicator confirming that said heartbeat monitoring system will receive sufficient power for a predetermined period of time once said weight sensing system determines that said baby is disposed upon said pillow.

30. The baby handling device, as described in claim 1, wherein said irregular star-shaped pillow further comprises a respiration monitoring system, said respiration monitoring system further comprising an alarm system to indicate absence of said baby's breathing.

31. The baby handling device, as described in claim 30, wherein said irregular star-shaped pillow further comprises a weight sensing system to determine if said baby is positioned upon said pillow and said respiration monitoring system should be activated.

32. The baby handling device, as described in claim 31, further comprising a battery life indicator, said battery life indicator confirming that said respiration monitoring system will receive sufficient power for a predetermined period of time once said weight sensing system determines that said baby is disposed upon said pillow.

33. The baby handling device, as described in claim 1, wherein said irregular star-shaped pillow further comprises a motion detection system, said motion detection system further comprising an alarm system to indicate absence of said baby's movement.

34. The baby handling device, as described in claim 33, wherein said irregular star-shaped pillow further comprises a weight sensing system to determine if said baby is positioned upon said pillow and said motion detection system should be activated.

35. The baby handling device, as described in claim 34, further comprising a battery life indicator, said battery life indicator confirming that said motion detection system will receive sufficient power for a predetermined period of time once said weight sensing system determines that said baby is disposed upon said pillow.

36. A baby handling device, comprising:
an irregular star-shaped pillow;
a removable, washable pillow cover, said cover being sized and shaped to fit over and extend from said irregular star-shaped pillow and providing at least two elongated star-point shaped extensions, said extensions being formed of flexible material and adapted to fold over and enclose at least a portion of two babies positioned on said cover;
an upper portion of said cover adapted to support and control movement of said babies' heads when said elongated star-point shaped extensions are wrapped around said babies and fastened to an outer surface of said cover; and
said cover having a closeable opening sized and shaped to permit insertion and removal of said pillow.

37. The baby handling device, as described in claim 36, wherein said irregular star-shaped pillow is formed of resilient material and further comprises:
a broad upper section sized and shaped to support said babies' heads;
a central point-shaped portion extending upwardly from a center point of said upper section, said central point-shaped portion adapted to lodge under an arm of a breast feeding mother;
first and second side sections, said side sections being joined to first and second ends of said upper section and being sized and shaped to support outer arms of said babies;
a center arm rest, said center arm rest being joined to a center point of a bottom edge of said upper section and being sized and shaped to support inner arms of said babies;
a lower section, said lower section being joined to said first and second side sections and being sized and shaped to provide a stop for said babies' feet, said stop preventing said babies from sliding downwardly from said center section;
said broad upper section, said side portions, said center arm rest and said lower section surrounding first and second center sections, said center sections providing support platforms for said babies and working with said broad upper section to control an inclination of said babies' heads when said babies are disposed on their backs upon said pillow.

38. The baby handling device, as described in claim 37, wherein said irregular star-shaped pillow further comprises first, second, third and fourth dividers, said dividers being disposed on either side of a center point of said upper section and serving to control positioning of said babies' heads on said upper section.

39. The baby handling device, as described in claim 37, wherein said irregular star-shaped pillow further comprises first and second depressions, said first and second depressions being disposed on either side of a center point of said upper section and serving to control positions of said babies' heads on said upper section to limit inclination of said babies' heads.

40. The baby handling device, as described in claim 37, wherein said irregular star-shaped pillow further comprises first and second point-shaped portions, said first and second point-shaped portions extending outwardly from said first and second ends of said upper section.

41. The baby handling device, as described in claim 37, wherein an included angle formed between said broad upper section and either of said first and second center sections is greater than or equal to 150 degrees.

42. The baby handling device, as described in claim 37, wherein said resilient material is selected from the group comprising:
cotton batting, polyester batting, foam rubber, memory foam, memory foam segments and an inflatable bladder.

43. The baby handling device, as described in claim 36, wherein said removable, washable pillow cover is formed of material selected from the group comprising:
terrycloth, cotton, polyester, cotton-polyester blends, wool, rayon, bamboo, satin weave fabrics and sateen weave fabrics.

44. The baby handling device, as described in claim 37, wherein said irregular star-shaped pillow further comprises at least one fastening device and said cover comprises at least one mating fastening device for securing said pillow within said cover.

45. The baby handling device, as described in claim 44, wherein said at least one fastening device is selected from the group comprising:
tie strings, hook and eye combinations, hooking and looping devices, buttons, snaps and zippers.

46. The baby handling device, as described in claim 37, wherein said irregular star-shaped pillow is formed of impermeable material.

47. The baby handling device, as described in claim 36, wherein said removable cover further includes a storage pocket.

48. The baby handling device, as described in claim 36, further comprising at least one point attachment device, said at least one point attachment device providing attachment for a distal end of each of said elongated star-point shaped extensions to at least one location on an exterior surface of said cover, thereby adapting said extensions to secure said babies in predetermined positions.

49. The baby handling device, as described in claim 48, wherein said at least one point attachment device in selected from the group comprising:
tie strings, hook and eye combinations, hooking and looping devices, buttons, snaps and zippers.

50. The baby handling device, as described in claim 48, wherein said at least one point attachment device is disposed to secure said babies in a first position, said first position attaching said extension at shoulder height for said babies, said first position constraining arms of said babies.

51. The baby handling device, as described in claim 48, wherein said at least one point attachment device is disposed to secure said babies in a second position, said second position attaching said extension at abdomen height for said babies, said second position permitting movement of arms of said babies.

52. The baby handling device, as described in claim 40, further comprising at least one accessory fastening device, said at least one accessory fastening device being attached to said cover where said cover extends over any of said central point-shaped portion and said first and second point-shaped portions of said irregular star-shaped pillow, said at least one accessory fastening device providing an attachment point for toys, pacifiers and other accessories.

53. The baby handling device, as described in claim 37, wherein said irregular star-shaped pillow further comprises an electrically operated vibrating element, said element causing said device to provide a soothing vibration to induce sleep in said baby.

54. The baby handling device, as described in claim 37, wherein said irregular star-shaped pillow further comprises at least one loudspeaker and electrically operated sound source, said sound source providing music to provide a calming environment for said baby.

55. The baby handling device, as described in claim 36, further comprising a combination fastening and carrying strap, said strap serving to hold the device in a compact bundle and to provide a carrying handle, said strap being attached to said removable cover with any of stitching, hook and eye combinations, buttons, snaps, looping and hooking fasteners and zippers.

56. The baby handling device, as described in claim 36, wherein said removable cover comprises a plurality of attachment devices, said attachment devices securing said elongated star-point shaped extensions about said irregular star-shaped pillow in a compact bundle.

57. The baby handling device, as described in claim 55, wherein said combination fastening and carrying strap provides a mounting for baby toys and accessories and is adapted to secure said babies to the irregular star-shaped pillow.

58. The baby handling device, as described in claim 36, wherein each of said elongated star-point shaped extensions of said cover is adapted to provide a privacy shield during nursing.

59. The baby handling device, as described in claim 37, further comprising a carrying bag, said bag being sized and shaped to enclose any of said removable, washable pillow cover, said irregular star-shaped pillow and baby supplies.

60. The baby handling device, as described in claim 55, further comprising a carrying strap.

61. The baby handling device, as described in claim 59, wherein said carrying bag further comprises at least one pocket.

62. The baby handling device, as described in claim 36, wherein said irregular star-shaped pillow further comprises a heartbeat monitoring system, said heartbeat monitoring system further comprising an alarm system to indicate absence of either of said babies' heartbeats.

63. The baby handling device, as described in claim 62, wherein said irregular star-shaped pillow further comprises a weight sensing system to determine if either of said babies is positioned upon said pillow and said heartbeat monitoring system should be activated.

64. The baby handling device, as described in claim 63, further comprising a battery life indicator, said battery life indicator confirming that said heartbeat monitoring system will receive sufficient power for a predetermined period of time once said weight sensing system determines that either of said babies is disposed upon said pillow.

65. The baby handling device, as described in claim 36, wherein said irregular star-shaped pillow further comprises a respiration monitoring system, said respiration monitoring system further comprising an alarm system to indicate absence of either of said babies' breathing.

66. The baby handling device, as described in claim 65, wherein said irregular star-shaped pillow further comprises a weight sensing system to determine if either of said babies is positioned upon said pillow and said respiration monitoring system should be activated.

67. The baby handling device, as described in claim 66, further comprising a battery life indicator, said battery life indicator confirming that said respiration monitoring system will receive sufficient power for a predetermined period of time once said weight sensing system determines that either of said babies is disposed upon said pillow.

68. The baby handling device, as described in claim 36, wherein said irregular star-shaped pillow further comprises a motion detection system, said motion detection system further comprising an alarm system to indicate absence of either of said babies' movement.

69. The baby handling device, as described in claim 68, wherein said irregular star-shaped pillow further comprises a weight sensing system to determine if either of said babies is positioned upon said pillow and said motion detection system should be activated.

70. The baby handling device, as described in claim 69, further comprising a battery life indicator, said battery life indicator confirming that said motion detection system will receive sufficient power for a predetermined period of time once said weight sensing system determines that either of said babies is disposed upon said pillow.

* * * * *